(12) United States Patent
Klebba et al.

(10) Patent No.: US 12,130,282 B2
(45) Date of Patent: Oct. 29, 2024

(54) UNIVERSAL FLUORESCENCE ASSAY OF HIGH AFFINITY LIGAND TRANSPORT

(71) Applicant: Kansas State University Research Foundation, Manhattan, KS (US)

(72) Inventors: Phillip E. Klebba, Manhattan, KS (US); Somnath Chakravorty, Buffalo, NY (US); Yan Shipelskiy, Holland, PA (US); Salete M. Newton, Manhattan, KS (US); Ashish Kumar, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 875 days.

(21) Appl. No.: 17/253,412

(22) PCT Filed: Jun. 18, 2019

(86) PCT No.: PCT/US2019/037760
§ 371 (c)(1),
(2) Date: Dec. 17, 2020

(87) PCT Pub. No.: WO2019/246118
PCT Pub. Date: Dec. 26, 2019

(65) Prior Publication Data
US 2021/0263014 A1   Aug. 26, 2021

Related U.S. Application Data

(60) Provisional application No. 62/686,464, filed on Jun. 18, 2018.

(51) Int. Cl.
*G01N 33/573* (2006.01)
*G01N 33/50* (2006.01)
*G01N 33/543* (2006.01)

(52) U.S. Cl.
CPC ... *G01N 33/5008* (2013.01); *G01N 33/54366* (2013.01); *G01N 2333/795* (2013.01)

(58) Field of Classification Search
None
See application file for complete search history.

(56) References Cited

U.S. PATENT DOCUMENTS

| | | |
|---|---|---|
| 10,604,782 B2 | 3/2020 | Klebba et al. |
| 2005/0287070 A1 | 12/2005 | Klebba et al. |
| 2012/0208744 A1 | 8/2012 | Postle |

FOREIGN PATENT DOCUMENTS

WO   2017004577   1/2017

OTHER PUBLICATIONS

International Search Report and Written Opinion in corresponding PCT/US2019/37760, dated Sep. 20, 2019.
Kadner, et al., "Mutual Inhibition of Cobalamin and Siderophore Uptake Systems Suggests Their Competition for TonB Function", Journal Bacteriology, Sep. 1995, 177 (17) 4829-4835.
International Search Report and Written Opinion dated Sep. 16, 2016, in PCT/US2016/040815, filed on Jul. 1, 2016.
Jordan, Lorne D. "Energy-dependent motion of TonB in the Gram-negative bacterial inner membrane," PNAS, Jul. 9, 2013, pp. 11553-11558; vol. 110, No. 28.
Kirkham, Lee-Ann S. "A practical method for preparation of pneumococcal and nontypeable Haemophilus influenzae inocula that preserves viability and immunostimulatory activity," BMC Research Notes 2013. 6:552.
Smallwood, Chuck R. "Concerted loop motion triggers induced fit of FepA to ferric enterobactin," J. Gen. Physical, vol. 144, 2014, No. 1, 71-80, The Rockefeller University Press.
Yep, Alejandra "Inhibitors of TonB Function Identified by a High-Throughput Screen for Inhibitors of Iron Acquisition in Uropathogenic *Escherichia coli* CFT073," mBio Mar./Apr. 2014 vol. 5. Issue 2. mbio.asm.org.
Bjarnason, Jaime "Genomic Profiling of Iron-Responsive Genes in Salmonella enterica Serovar Typhimurium by High-Throughput Screening of a Random Promoter Library,"Journal of Bacteriology, Aug. 2003, pp. 4973-1982, vol. 185, No. 16, American Society for Microbiology.

*Primary Examiner* — Jennifer E Graser
(74) *Attorney, Agent, or Firm* — Hovey Williams LLP; Crissa A. Cook

(57) ABSTRACT

A universal bacterial assay and kit for detecting and monitoring changes in concentration of a target analyte in solution. The assay relies on an engineered high affinity protein-based sensor with a detectable label that has high specificity to a target analyte, typically a ligand or metallated complex, and can be used to spectroscopically monitor interaction of the target analyte with a test bacterial strain. The sensors can be in the form of living, transport-deficient bacterial cells expressing the engineered high affinity protein, or in the form of purified proteins themselves. The system can further be used to screen candidate compounds for interference with the binding and uptake of such analytes by bacterial cells, which is useful in investigation of new classes of antibiotics.

30 Claims, 10 Drawing Sheets

UNIVERSAL FLUORESCENCE ASSAY OF HIGH AFFINITY LIGAND TRANSPORT

CROSS-REFERENCE TO RELATED APPLICATIONS

The present application is the U.S. National Stage of International Patent Application No. PCT/US2019/037760, filed Jun. 18, 2019, which claims the priority benefit of U.S. Provisional Patent Application Ser. No. 62/686,464, filed Jun. 18, 2018, entitled UNIVERSAL FLUORESCENCE ASSAY OF HIGH AFFINITY LIGAND TRANSPORT, each of which is incorporated by reference in its entirety herein.

FEDERALLY SPONSORED RESEARCH OR DEVELOPMENT

This invention was made with government support under grant #R21 AI1 15187 awarded by the National Institutes of Health. The government has certain rights in the invention.

BACKGROUND OF THE INVENTION

Field of the Invention

The present invention relates to high affinity protein-based assays for detecting and monitoring analyte transport in a variety of Gram-negative and Gram-positive bacteria.

Description of Related Art

Sensitive assays of biochemical specificity, affinity, and capacity are valuable both for basic research and drug discovery. Further, there remains an ongoing need for discovery and development of antibiotic drugs for use especially against multidrug-resistant bacteria. Increasing antibiotic resistance necessitates new agents to combat infectious bacteria. Universal sensors and assays for high throughput screening related to prokaryotic ligand acquisition systems would provide advantages over existing screening systems.

SUMMARY OF THE INVENTION

The present disclosure is concerned with universal bacterial assays for detecting and monitoring changes in concentration of a target analyte (ligand) in solution. The assays generally comprise creating a reaction solution comprising a high affinity protein-based sensor and a test bacteria dispersed in an aqueous solution. The sensor comprises a bacterial high affinity binding protein engineered with a detectable label that generates a detectable signal, and is characterized by specific binding with the target analyte of interest for the particular assay. The target analyte is added to the reaction solution, and is typically a metal, a source of metal, or a metallated complex. The reaction solution is then exposed to an energy source to generate the detectable signal, and the changes (if any) in the detectable signal are detected. These changes correspond to interaction of the test strain with the target analyte. As described in more detail below, the assay is typically monitored over time and various readings are taken of the detectable signal at various time points (i.e., before addition of analyte, after addition of analyte, and after potential recovery/transport by the test strain).

In one aspect, the disclosure concerns fluorescent sensors that monitor high affinity binding reactions, which can be used to study iron acquisition by ESKAPE bacteria, that are frequently responsible for antibiotic-resistant infections. The sensors include living cells, such as the TonB transport deficient E. coli cells described herein or purified protein Hbp2, each of which have been engineered with a fluorescent reporter moiety, and function as universal sensors of extracellular iron in different forms: FeEnt, Fc, and hemin, respectively. By introducing site-directed Cys residues in bacterial iron transporters and modifying them with maleimide fluorophores, we generated living cells or purified proteins that bind but do not transport target compounds. These constructs sensitively detected ligand concentrations in solution, enabling accurate, real-time spectroscopic analysis of membrane transport by other cells. The efficacy of these "fluorescent decoy" (FD) sensors was assessed by characterizing active iron transport in the ESKAPE bacteria: FD sensors monitored uptake of both ferric siderophores and hemin by the co-cultured pathogens. An FD sensor for a particular ligand was universally effective in observing the uptake of that compound by all organisms tested. The sensors are also adaptable to microtiter format, where they allow high-throughput screens for chemicals that block iron uptake, without genetic manipulations of the test bacteria. Hence, screening assays with FD sensors facilitate studies of mechanistic biochemistry, as well as discovery of chemicals that inhibit prokaryotic membrane transport. With appropriate design, FD sensors are potentially applicable to any prokaryotic high affinity ligand transport process.

The invention is also concerned with kits for conducting universal bacterial assays for detecting and monitoring changes in concentration of a target analyte in solution. The kits generally comprise high affinity protein-based sensors comprising a high affinity binding protein engineered with a detectable label that generates a detectable signal, wherein high affinity binding protein is a bacterial protein specific for a metallated target analyte. The kit can also include an amount of the target analyte optionally provided (or it can be obtained from a third party or otherwise provided on the user's end). Likewise, the kit can include the test bacteria strain (or it can be obtained from a third party or otherwise provided on the user's end). The kit will also include instructions for creating a reaction solution with the high affinity protein-based sensor, test bacteria strain, and target analyte, as well as instructions for exposing the reaction solution to an energy source to generate a detectable signal along with instructions for detecting changes in the detectable signal in the reaction solution over time to determine the interaction of the test bacterial strain with the target analyte. In some embodiments, the kit may also include candidate compounds or associated instructions for using various candidate compounds with the assay.

Figure 1:
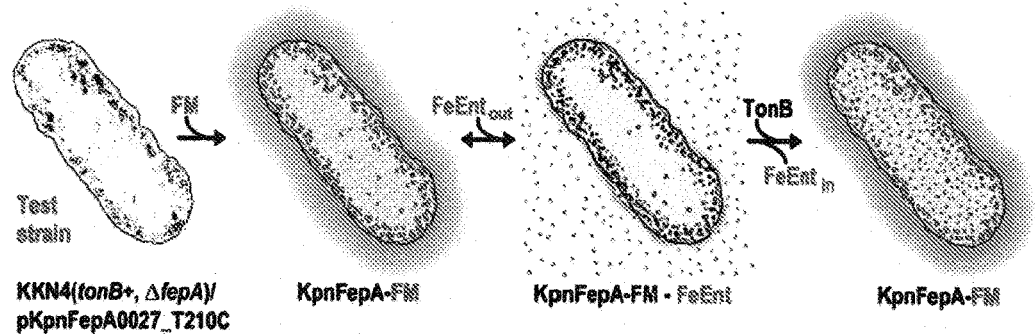
FIG. 1 illustrates fluorescence observations of membrane transport of two different assay designs: (A) Species-specific assay design. The target organism (e.g., K. pneumoniae) contains a Cys substitution for a surface-exposed residue in a TonB-dependent transporter (KpnFepA_T210C), labeled with FM. Fluorescence emissions depict FeEnt binding and TonB-dependent FeEnt transport in K. pneumoniae. (B) Universal FD sensor assay design. The fluorescence of a TonB-deficient E. coli "sensor" strain OKN13 (ΔtonB, ΔfepA)/pEcoFepA_A698C-FM reflects TonB-dependent FeEnt transport by a second test strain (e.g., *K. pneumoniae* strain Kp52.145) in the same solution.
Figure 1:
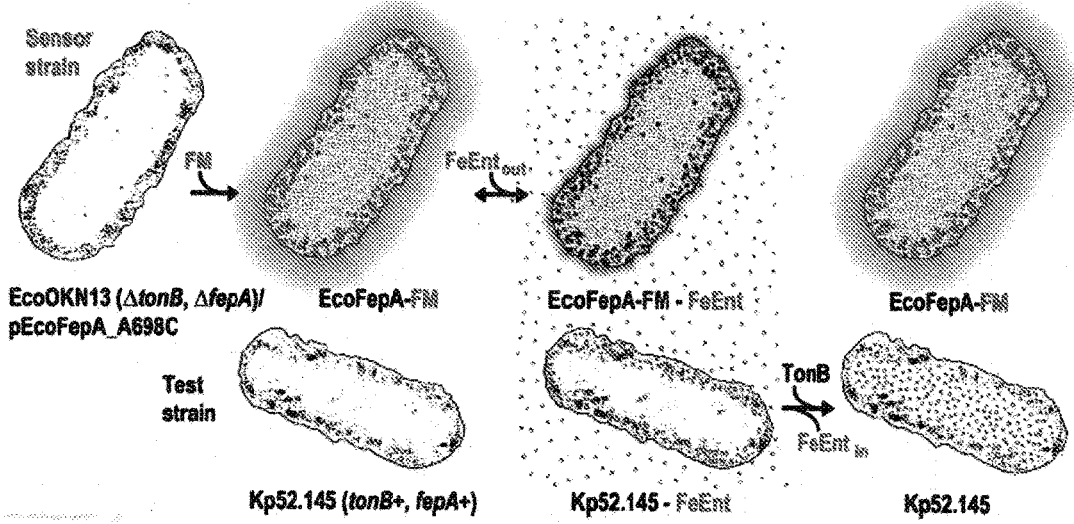

The experiment revealed that site S286C (yellow) was optimum for observation of vitamin B12 binding. Panel D shows the uptake of vitamin B12 by Gram (−) ESKAPE pathogens and *E. coli*, using residue S286C as a universal fluorescent sensor.

DETAILED DESCRIPTION

The present invention is concerned with engineered high affinity protein-based sensors and associated assays for detecting and monitoring changes in concentration of a target analyte in solution, and particularly ligands, siderophores, and metallated complexes in the nanomolar concentration range. The sensors and assays can be used to detect and identify specificities, affinities, and kinetic attributes of a transport system for a single ligand or a family of ligands in a test bacteria strain. Further, the sensors and assays can be used to detect and identify compounds effective against Gram-negative and/or Gram-positive bacteria, such as by inhibiting transport of various analytes. It will be appreciated that inhibitor compounds may completely prevent transport of target analytes/complexes by the bacterial cells; however, a compound may also be considered an "inhibitor" if it hinders, restrains, or only partially prevents transport of the target analyte/complex by the cell. The sensors and assays are adaptable to a high-throughput screening format.

In general, the sensors comprise a high affinity binding protein engineered with a detectable label (i.e., molecular reporter moiety). Exemplary detectable labels include fluorescent dyes or fluorophores. Once labeled, these sites become reporter groups (i.e., fluorescent probes) that convey information about the biochemical activities of co-cultured bacteria in the presence of the target analyte/ligand. Hence the experimental system spectroscopically reports on when the analyte binds to the sensor (thus quenching the detectable label), and when the analyte is taken up and transported by co-cultured bacteria (thus depleting it from the solution and restoring the fluorescent signal of the sensor).

As used herein, references to "high affinity" binding protein means a protein with a strong affinity for its target analyte, characterized by a binding reaction with an equilibrium dissociation constant ($K_d$) value in the nanomolar range (<1000 nM) or below, preferably 300 nM or less, preferably 100 nM or less, more preferably 50 nM or less, and even more preferably 15 nM or less (0.1-15 nM), and even more preferably 10 nM or less (0.1-10 nM). The dissociation constant corresponds to the analyte (ligand) molar concentration at which half of the proteins are occupied at equilibrium, that is, the molar concentration of analyte at which the molar concentration of protein with analyte bound equals the molar concentration of protein with no ligand bound. The smaller the dissociation constant, the more tightly bound the analyte is, and the higher the affinity between analyte and protein. For example, an analyte with a nanomolar (nM) dissociation constant binds more tightly to a particular protein than an analyte with a micromolar (µM) dissociation constant. In general, such proteins are typically part of bacterial transport systems for uptake of various critical elements, nutrients, etc. from medium into the cell. As such, these transport systems are ideal targets for developing new antimicrobial agents.

In one or more embodiments, the engineered high affinity binding protein is a bacterial membrane protein (e.g., Gram (−) outer membrane transporter or Gram(+) lipoprotein anchored on the membrane) with high affinity for binding its target analyte in solution. In one or more embodiments, the sensor is provided in the form of the engineered high affinity binding protein itself. In one or more embodiments, the sensor is provided in the form of a transport-deficient bacterial cell comprising the engineered high affinity binding protein expressed on its outer membrane surface. Exemplary bacteria for use as the sensor include *Escherichia coli*, *Acinetobacter baumannii*, *Klebsiella pneumoniae*, *Pseudomonas aeruginosa* and other microorganisms with high affinity for particular analytes. In general, when intact bacteria are used, they are transport-deficient bacteria. The bacterium may have a native deficiency in its ability to transport the particular analyte/ligand of interest, or may be engineered to have a defective transport mechanism for the target. In other words, in the context of the current disclosure, the cell-based assays utilize bacteria capable of binding the target analyte with specificity, but incapable of transport and uptake of the analyte. As such, the bacteria may be considered physiologically "inert," as lacking active transport functions at least for the target analyte. Examples include TonB-deficient bacteria lacking active iron transport capabilities in iron assays. In this manner, the analyte may be otherwise taken up by co-cultured bacteria and scavenged from the sensor thereby restoring its detectable signal in the assay.

Examples of high affinity binding proteins include EcoFepA, EcoFhuA, EcoBtuB, KpnIutA, KpnIroN, LmoHbp2, CcrHutA. These proteins are binding proteins for siderophores (ferric enterobactin, ferrichrome), vitamin B12, and hemin. In one or more embodiments, the protein is genetically-engineered or mutated, wherein the mutation comprises or consists of at least one amino acid residue of the native (chromosomal) protein substituted with a cysteine residue to generate the mutated protein. In one or more embodiments, the cysteine substitution results in a "single accessible cysteine" residue, which means that the location of the inserted cysteine residue being presented outwardly from the surface of the bacterial membrane or folded protein, such that it is "accessible" to react for labeling.

Accordingly, exemplary amino acid residues to be targeted for substitution should meet at both of the following criteria: (1) the targeted amino acid forms part of an outer loop of the native protein (so that the mutated cysteine residue will be outwardly presented); and (2) mutation of the targeted amino acid does not impair the analyte binding capabilities of the protein. In general, the targeted amino acid residues for mutation (and subsequent labeling) are those in the native protein with small side chains that are localized on the cell surface or outwardly presented on the folded protein. It will be appreciated that a protein native to the engineered bacteria may be altered in this manner (chromosomal modification). Alternatively, the engineered bacteria may be modified to express a non-native protein (e.g., a homologous binding protein from a different bacterial species) that has been modified to include the cysteine substitution for labeling (again provided that the binding capabilities are not impaired) (plasmid-mediated modification).

The specific mutated residue and target residue position will depend on the bacteria or protein used for the sensors. For FepA, exemplary native amino acids for targeted substitution include serine, glutamic acid, aspartic acid, alanine, and threonine. For example, when *E. coli* is the sensor bacteria, suitable native FepA residues targeted for cysteine substitution (and subsequent labeling) include residues 216, 271, or 698. Likewise, exemplary residues for substitution in *A. baumannii* FepA sensors include residues 278, 561, or 664. Exemplary residues for substitution in *K pneumoniae* FepA sensors include 210. Exemplary residue substitutions in *E. coli* for FhuA sensors include residues 396. Exemplary residue substitutions in Hpb2 protein-based sensors include 154.

It will be appreciated that the techniques illustrated in the working examples can be used to identify additional residues for substitution (and subsequent labeling) in other proteins and bacteria. Various known approaches can be used to engineer the proteins and bacteria to obtain the cysteine substitution. Further, it will be appreciated that wild type proteins and bacteria can be used to develop the sensors, the proteins and bacteria sensors may include other modifications in addition to the cysteine substitution described here, with the proviso that the native target analyte binding capabilities of the bacteria or protein are not impaired.

As noted, the high affinity binding protein is engineered for labeling with a suitable reporter moiety. In general, this involves incubating the engineered protein (or bacteria) with the selected fluorophore for a sufficient period of time, and under sufficient conditions to react with the free cysteine residue on the engineered protein. Preferably, the fluorophore is covalently attached to the engineered cysteine residue. In one or more embodiments, the fluorescent dye is a chemically-reactive derivative of fluorescein. Exemplary fluorophores include maleimide fluorophores, such as fluorescein maleimide, CPM (7-Diethylamino-3-(4'-Maleimidylphenyl)-4-Methylcoumarin), Alexa Fluors 488, 546, 555, 647, 680, and 720 and the like. In one or more embodiments, the fluorophore is incubated with the engineered protein (or bacteria) in phosphate buffer for at least about 5 min., and preferably from about 5 min. to about 15 min., at a temperature of from about 0° C. to about 37° C., and a pH ranging from about 6.5 to about 6.8. The labeling reaction is then quenched, and the labeled proteins or cells are washed. The labeled cells or proteins are then suspended in an aqueous solution. Exemplary aqueous solutions include solutions that are non-toxic to cells, and help maintain a neutral pH of the reaction solution in order not to destroy the sensor protein or cell and maintain the osmolarity of the cells. For example, buffer solutions including buffered saline solutions, such as phosphate buffered saline (PBS), are preferred aqueous solutions for used in the invention.

In one or more embodiments, the engineered high affinity protein-based sensors are then used directly in the assay or preserved for later use. In one or more embodiments, the engineered high affinity protein-based sensors are suspended in a buffer solution along with a cryoprotectant, such as DMSO and/or glycerol, followed by cryopreservation of the labeled cells for future use. In one or more embodiments, cell-based sensors can be cryopreserved for at least about 2 weeks and conceivably indefinitely before use in the assay. Likewise, because the sensor proteins can be expressed from plasmids, engineered sensor strains that host them may be centrally stored and distributed to any interested researcher.

In one or more embodiments, the assay comprises preparing a reaction solution comprising the engineered high affinity protein-based sensors and a test strain of bacteria. The analyte or ligand of interest is then added to the reaction solution and the interaction of the analyte with the test strain (if any) is detected. Thus, assays can be designed by pairing a sensor having high affinity binding for the analyte of interest, and detecting changes in the reaction solution over time, depending upon whether the test strain also interacts with the analyte of interest. The assay may also involve including a candidate compound in the reaction solution to detect the effect (if any) of the candidate compound on the interaction of the test strain with the analyte of interest. Exemplary "candidate compounds" include any compound suspected of or having potential as a specific inhibitor of uptake of the analyte, as well as compounds that block uptake for other reasons, such as the abrogation of a biochemical mechanism. Such compounds constitute new candidates for therapeutic applications against bacterial pathogens.

The reaction solution generally further comprises at least one nutrient (i.e., carbon source) dispersed in the aqueous solution to support bacterial cell functioning in the reaction solution. Exemplary nutrients will depend upon the particular bacteria used, and include glucose, sodium acetate, succinate, and the like. The reaction solution is formed in a reaction vessel. In one or more embodiments, the reaction vessel is a microwell. In one or more embodiments, the microwell is part of a multi-well array in a microplate (aka microtiter plate). The plates may include 96, 384, or 1536, etc., wells disposed across the surface of the plate substrate, and generally arranged in a rectangular matrix. In general, the diameter, depth and spacing of the microwells in the plate can vary. In one or more embodiments, the reaction vessel has a working volume of 300 µL or less. It will be appreciated that the "working volume" of the reaction vessel is less than its total volume, and refers to the recommended volume to be utilized in individual vessels for the reaction solution, to avoid overflowing the vessel's total capacity. In one or more embodiments, the reaction vessel has a working volume of 75 µL or less. In one or more embodiments, the reaction vessel has a working volume of from about 25 µL to about 300 µL. Thus, the reaction solution volume in the inventive assay will comprise less than about 300 µL total solution, preferably from about 20 to about 300 µL, and more preferably from about 25 to about 300 µL. It will be appreciated that an advantage of the inventive assays is miniaturization of the biochemical system to function in small volumes (≤300 µL), which allows the use of multi-compartment microtiter plates (e.g., 96- or 384-well plates). This adaptation of the methodology makes it compatible with high-throughput screening of chemical libraries to find inhibitors of analyte uptake.

The total cell density in the reaction solution in each reaction vessel may vary. In general low turbidity (dilute) reaction solutions are desired. In other words, the total cell density is preferably adjusted such that an adequate quantity of cells are present in each reaction vessel to generate a detectable quenching/unquenching reaction; however, an excess concentration of cells in the reaction solution is counterproductive in that it can cause adjacent cells to physically block the detectable signal from the reaction vessel. In one or more embodiments, total cell density in the reaction solution ranges from about $5\times10^6$ to about $5\times10^7$ cells/ml, preferably from about $5\times10^6$ to about $3\times10^7$ cells/ml, and more preferably from about $5\times10^6$ to about $2.5\times10^7$ cells/ml. In one or more embodiments, the total cell density is about $2.5\times10^7$ cells/ml or less. Optical density of the reaction solution can also be used to adjust the reaction solution cell concentration. Advantageously, the inventive methods can be used with cryopreserved sensor cells. It will be appreciated that in the case of cryopreserved cells, the cells will be thawed and subjected to appropriate post-thawing protocols before use in the assay (e.g., centrifugation and washing to remove cryoprotectant).

Once the engineered high affinity protein-based sensors and test strain of bacteria are mixed in solution, the target analyte (or source of analyte) of interest is added to the reaction solution. A variety of target analytes can be used that are relevant for understanding bacterial interaction and reliance on such analytes. Exemplary analytes include iron or iron complexes (chelated iron: siderophores such as FeEnt, Fc, ferric aerobactin, etc., or hemin), as well as other metallated complexes, such as vitamin B12, and similar high-affinity metal ligands. In one embodiment, the analyte is added to the reaction solution, which is then incubated at about 37° C. under stirring. In general, from about 1 nM to about 1 uM of the analyte is added to the solution.

In certain embodiments, the chemical compound of interest (aka candidate compound) may first be added the reaction solution in the reaction vessel, followed by addition of the analyte. In one or more embodiments, a plurality of candidate compounds can be assayed. For example, the reaction solution containing the sensor and test strain is distributed into a plurality of reaction vessels, such as a plurality of microwells in a microtiter plate. A plurality of candidate compounds are added to respective reaction vessels. In some cases, each reaction vessel contains a different candidate compound. In some cases, the same candidate compound can be added to a subgrouping of reaction vessels to provide an averaged result for that candidate compound across multiple reaction solutions. For example, one candidate compound can be added to a first quadrant of the array of microwells on a microtiter plate, while a second candidate compound can be added to a second quadrant of an array of microwells on a microtiter plate. In addition, it will be appreciated that different test strains can be used in the reaction solutions across a multi-well plate. That is, a given micro-titer plate does not necessarily have to assay the same test strain in every microwell, but different test strains may be present in respective microwells. Further, different fluorophores can be associated with different engineered proteins to give off discernable color variations among the detectable signals. Various combinations of types of sensors, test strains, and candidate compounds may be used, depending upon the desired design of the assay and target analyte to be studied, as will be appreciated by those in art.

Regardless of the embodiment, once the analyte is added, the assay is then monitored over time. More specifically, the detectable label on the engineered high affinity protein generates a signal that can be detected, and which changes over time depending upon the interaction (or lack thereof) of the target analyte and the test strain. In general, the assay is observed or the plate is read before and after the addition of the analyte (and optional candidate compound) to the reaction solution, and after fluorescence recovery (transport of the analyte) if it occurs. In particular, in the case of fluorescent labels, the assay solution is excited at the appropriate wavelength(s) and then observed for potential fluorescence quenching that occurs upon binding of the analyte to the sensor, and then un-quenching (rebound) as the test strain of bacteria depletes the analyte from solution by transport.

For example, a first fluorescence reading is taken of the reaction solution before addition of the analyte. A second fluorescence reading is then taken of the reaction solution immediately (i.e., about 1 second to about 10 seconds) after addition of the analyte. A third fluorescence reading is then taken at least 5 minutes after addition of the analyte, preferably from about 5 to about 45 minutes after addition of the analyte, and conceivably from about 5 to about 150 minutes after addition of the analyte. Various instruments are available for detecting the fluorescence signal, including commercially-available fluorometers. The assays can be optimized to reduce interference with impurities in the reaction solution, including unintentional or incidental amounts of metal complexes and the like introduced during the process or produced by the cells themselves. For example, the cells can be washed before analysis to remove any siderophores that may have been produced by the cells in response to iron-deficient conditions. The assay duration is kept relatively short (~45 min. or less) to further minimize siderophore production by the test strain. Moreover, it is desirable to use buffer systems that are substantially free of adventitious metal complexes and/or metabolites to constrain biosynthesis by the test strains.

In one or more embodiments, if a candidate compound is added to the reaction solution, the candidate compound may be an inhibitor of binding and/or transport of the target analyte in the test strain. As such, the test strain may not be able to deplete the analyte from solution and an unquenching (recover) is not observed. Some inhibitors may only partially inhibit transport, which is detectable based upon a change in the kinetics or intensity of the fluorescence rebound in the sensor as the test strain slowly depletes the analyte. Thus, the assay provides for real-time sequential quenching and un-quenching of fluorescence intensity that inversely correlates with iron transport by the test strains. This novel technique can be used to screen for candidate compounds with antimicrobial potential against any variety of both Gram-negative and Gram-positive bacteria. Secondary screenings can also be carried out to verify the inhibitory potential of compounds identified by the novel assays, as described in detail in the working examples.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Introduction

Sensitive assays of biochemical specificity, affinity and capacity are valuable for basic research and drug discovery and in many experimental settings, including biochemical measurements of living cells, and the discovery of new therapeutic compounds. At present a need exists for new antibiotics against multidrug-resistant bacteria, because without them, treatment options for many infections will dwindle. Gram (−) strains cause about two-thirds of the mortality from bacteria in US hospitals, and up to 20% of these strains are resistant to all antibiotics. The World Health Organization identified the Gram (−) ESKAPE pathogens *Klebsiella pneumoniae, Acinetobacter baumannii, Pseudomonas aeruginosa* and *Enterobacter* spp., as well as carbapenem-resistant (CRE) strains of *K. pneumoniae* and *Escherichia coli*, as critical targets for drug discovery. Compounds that inhibited bacterial cell envelope processes were once the most potent antibiotics, but now their efficacy has diminished as a result of bacterial adaptation. Gram (−) bacterial antibiotic resistance largely originates from cell envelope physiology: the outer membrane (OM) excludes large or hydrophobic compounds, periplasmic enzymes degrade or inactivate chemicals that breach the OM barrier, and inner membrane (IM) pumps expel hydrophobic molecules, including antibiotics. Similar processes in Gram (+) bacteria heighten the need for new treatments of bacterial infections.

Nevertheless, bacterial pathogens face nutritional obstacles in human and animal hosts that we may exploit against them. Iron, for example, is a cofactor in many biochemical pathways, including catabolism, DNA synthesis and bioenergetics. Iron-deprivation retards bacterial growth; iron availability promotes it. Animals sequester iron in transferrin, lactoferrin and ferritin to minimize bacterial infections. But, microbial siderophores capture the metal from host proteins, and ferric siderophores then enter bacterial cells through high affinity acquisition systems. The balance of these competing processes influences the outcome of infection, so bacterial iron uptake systems are potential targets for antibiotics.

Toward that end we studied the ferric enterobactin (FeEnt) uptake system of Gram (−) bacteria. FeEnt enters through the OM protein FepA, that selectively binds and transports it. The uptake reaction requires the additional cell envelope protein TonB, so FepA and other OM proteins in this superfamily are called "TonB-dependent transporters" (TBDT). TonB action, that is proposed to transmit the potential energy of the electrochemical proton gradient across the IM to TBDT in the OM, underlies the active intake of bound iron complexes. TonB is ubiquitous in Gram (−) bacteria, and a determinant of their pathogenesis. Iron acquisition through TBDT contributes to the invasiveness of the Gram (−) ESKAPE pathogens, the determination of their ultimate localization in human and animal tissues, and the overall outcome of their infections.

Figure 2:
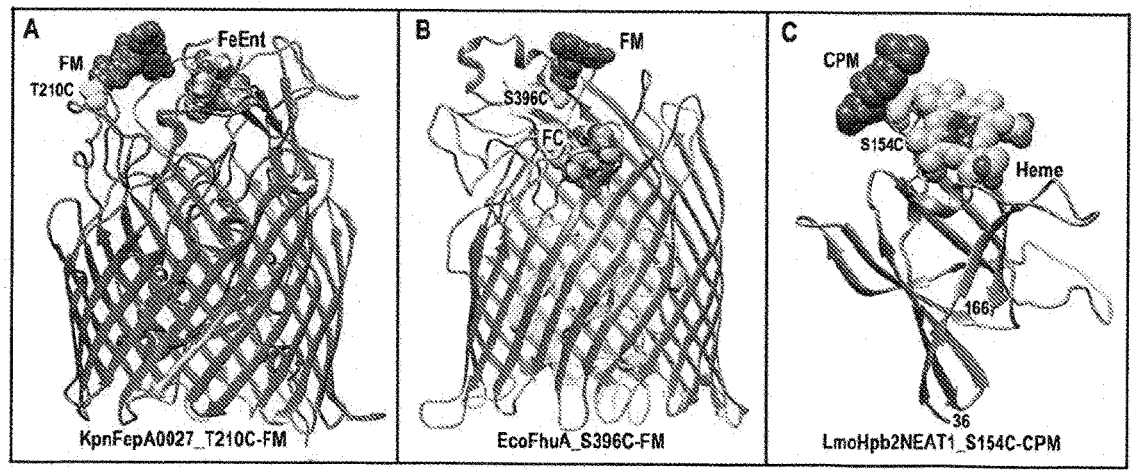
FIG. 2. FD sensor and predictive binding for: A. Kpn-FepA-FM; B. EcoFhuA-FM; C. LmoHbp2-CP.

We previously designed fluorescence methods that monitored high affinity ligand binding and uptake. By genetically engineering FepA and then labeling it with fluorescein maleimide (FIG. 1; FIG. 2), we created a sensor that reflected [FeEnt] in the environment. When FeEnt bound to FepA-FM it quenched its fluorescence. Quenching originated from binding-induced conformational motion in the external loops of FepA, that subjected attached fluorophores to collisions with other residue side chains or elements of protein structure, or increased interactions with the aqueous environment. When cellular uptake depleted FeEnt from solution, fluorescence rebounded. Consequently, FepA-FM tracked the binding and transport of FeEnt by living bacteria.

In this report we created both species-specific and generic fluorescence spectroscopic assays (FIG. 1 and FIG. 2) that measure ligand uptake. Universal sensors were designed as follows. From the coordinates of EcoFepA (1FEP) we used MODELLER of CHIMERA (UCSF) to predict the structure of KpnFepA0027, and selected residue T210 for substitution with Cys and fluoresceination. FeEnt binding quenches fluorescence of cells expressing KpnFepA-FM. From the coordinates of EcoFhuA (1BY5) we selected residue S396 for substitution with Cys and fluoresceination. Fc binding quenches fluorescence of cells expressing EcoFhuA-FM. From the coordinates of LmoHbp2-NEAT2 (4MYP) (35) we used MODELLER of CHIMERA to predict the structure of NEAT1, and identified S154 (yellow), near the heme binding site, for substitution with Cys and modification by CPM (light green). Hemin binding quenches fluorescence of purified LmoHbp2_S154C-CPM (infra).

Fluorescently labeled, binding-competent, but transport-defective cells, and fluorescently labeled purified proteins, were key innovations in these experiments. Such genetically engineered cells or proteins comprise "fluorescent decoy" (FD) sensors, that report ligand concentrations in solution and monitor transport of the same ligand by other cells. We illustrate these applications by observations of iron transport activity through Gram (−) bacterial TBDTs, and Gram (+) bacterial NEAT domain-dependent hemin (Hn) uptake systems. Both high affinity pathways function at nanomolar concentrations, and both contribute to bacterial colonization of eukaryotic hosts. We adapted these fluorescence tests to microtiter high-throughput screening format, to enable discovery of inhibitors that retard iron acquisition, and thereby prevent bacterial growth and pathogenesis.

Results

Figure 3:
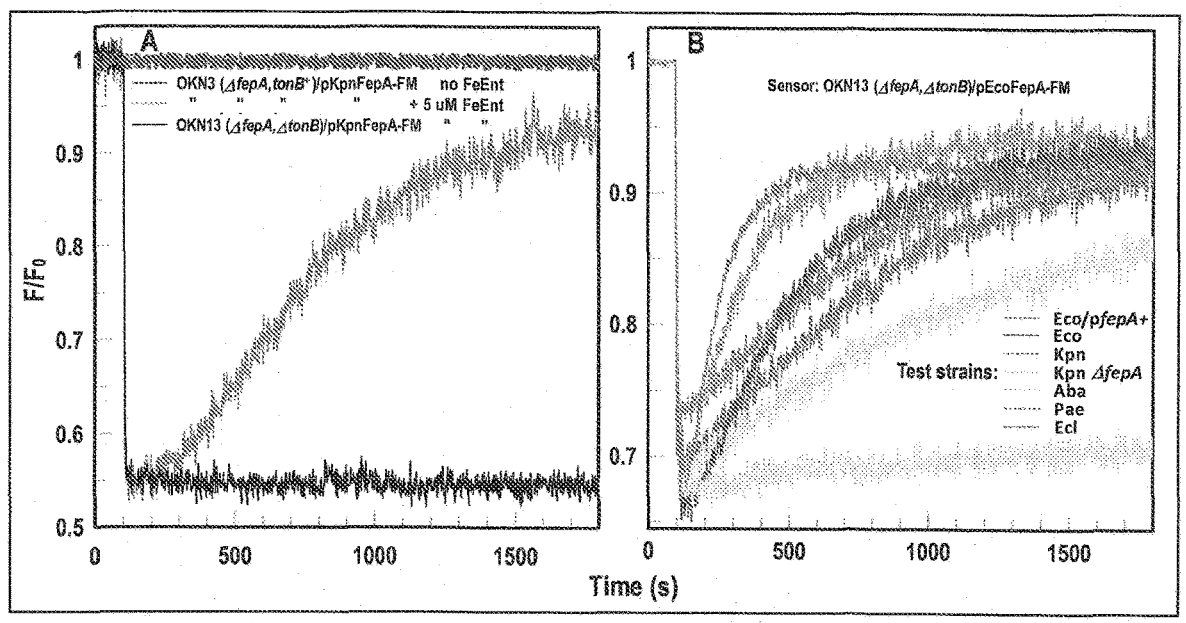
FIG. 3. FD sensor analysis of FeEnt acquisition by ESKAPE pathogens. (A) *E. coli* OKN3 (ΔfepA) expressing KpnFepA-FM The tracings show emissions of living cells in the absence (dark blue) or presence (dark red or black) of FeEnt. (B) Universal fluorescence assay of FeEnt uptake: sensor strain OKN13/pEcoFepA-FM. The panels show the results of single representative experiments that were performed in triplicate, from which we calculated and plotted the mean values. Standard deviations of the mean measurements (data not shown) were 1.7-2.7%.

Universal fluorescence sensor of FeEnt acquisition. We originally devised species- or transporter-specific fluorescent assays of FeEnt uptake for FepA of *E. coli* and *A. baumannii*; the same approach was effective for FepA of *Klebsiella pneumoniae* (FIG. 3). We cloned and genetically engineered KpnfepA of strain Kp52.145 to enable site-directed fluoresceination in its native cellular (i.e., *K. pneumoniae*) environment, and in *E. coli*. These studies compared the acquisition of FeEnt by FepA orthologs in different bacteria.

TABLE 1

Bacterial strains, plasmids, and fluorescent proteins

Bacterial strains

| Organism | Genotype/locus |
| --- | --- |
| *E. coli* OKN1 | trp, entA, ΔtonB |
| *E. coli* OKN3 | trp, entA, ΔfepA |
| *E. coli* OKN13 | OKN1, ΔfepA |
| *K. pneumoniae* Kp52.145 | prototypic *K. pneumoniae* |
| *K. pneumoniae* Kp52.145 KKN4 | ΔentB, ΔfepA0027, ΔfepA1658, ΔfepA1658, |

Plasmids and plasmid-derived, fluorescently labeled proteins

| Plasmid | Locus | Protein | Abbreviation |
| --- | --- | --- | --- |
| pHSG575 | empty vector | NA | NA |
| pITS23 | pHSG575, ecofepA+ | EcoFepA | EcoFepA |
| pEcoFepA_A698C | pHSG575, ecofepA_A698C | EcoFepA_A69BC-FM | EcoFepA-FM |
| pITS11 | pHSG575, ecofhuA+ | EcoFhuA | EcoFhuA |
| pEcoFhuA_D396C | pHSG575, ecofhuA_D396C | EcoFhuA_D396C-FM | EcoFhuA-FM |
| pKpnFepA+ | pHSG575, kpnfepA+ | KpnFepA | KpnFepA |
| pKpnFepA_T210C | pHSG575, kpnfepA_T210C | KpnFepA_T210C-FM | KpnFepA-FM |
| pAbaFepA_A598C | pHSG575, abafepA_A598C | AbaFepA_A598C-FM | AbaFepA-FM |
| pAT28 | empty vector | NA | NA |
| pLmoHbp2_D154C | pAT28, lmoHbp2_D154C | LmoHbp2_D154C-CPM | LmoHbp2-CPM |

As for FepA of *E. coli* and *A. baumannii*, FM exclusively labeled KpnFepA in living cells (FIG. 2, 4; see Table 1 for strains, plasmids and abbreviations), and the fluoresceinated GM protein detected and quantified its ligand, FeEnt. Binding of FeEnt to KpnFepA-FM quenched its fluorescence, but as the transporter's activity depleted FeEnt from solution, fluorescence intensity rebounded (FIG. 2A). In tonB+ cells (dark red), FeEnt binding to KpnFepA-FM (at 100 s) quenched emissions, but subsequent uptake depleted FeEnt from solution, restoring fluorescence. In TonB-deficient *E. coli* OKN13 ($\Delta$fepA, $\Delta$tonB)/pKpnFepA-FM; black), that cannot transport FeEnt, quenching occurred, but not recovery. Thus, by the species-specific approach EcoFepA-FM, AbaFepA-FM and KpnFepA-FM (FIG. 3A) all detected FeEnt binding and reflected its transport. Each of these transporters requires TonB action for FeEnt uptake: its absence or inhibition prevented fluorescence recovery. By engineering the individual transporters of specific bacteria we observed, monitored and characterized their TonB-dependent iron uptake processes.

The species-specific method was sensitive and accurate, but genetic and biochemical manipulations of ESKAPE organisms and other pathogens are technically challenging and potentially hazardous. We discovered a modification that extends the scope of the assay to allow observations of FeEnt uptake by other organisms, including clinical isolates, without genetically engineering them. TonB-deficient Gram (−) cells adsorb ferric siderophores and other metal complexes (e.g., vitamin $B_1$), but cannot transport them. Thus, FeEnt bound to *E. coli* OKN13 ($\Delta$tonB, $\Delta$fepA)/pEcoFepA-FM, quenching its fluorescence, but the strain's TonB-deficiency prevented FeEnt internalization (FIGS. 1B, 3B). The placement of EcoFepA-FM in OKN13 transformed the cell into an FD sensor, whose emissions inversely related to [FeEnt]. The transport defective, physiologically inert, fluorescent $\Delta$tonB bacteria detected the presence and concentration of FeEnt. When this strain cohabited an environment with other bacteria it reflected their uptake of FeEnt. Solution levels that saturated EcoFepA-FM ($K_d$=0.2 nM) quenched its fluorescence, but if the ambient [FeEnt] decreased from its uptake by other cells, then fluorescence rebounded. The upshot is that the $\Delta$tonB FD sensor cells monitored FeEnt transport by wild isolates of *K. pneumoniae, A. baumannii, P. aeruginosa* or *E. cloacae* (FIGS. 1, 3B). The FD sensor observed FeEnt uptake by all the organisms we tested, reflecting TonB action in the pathogens.

Figure 5:
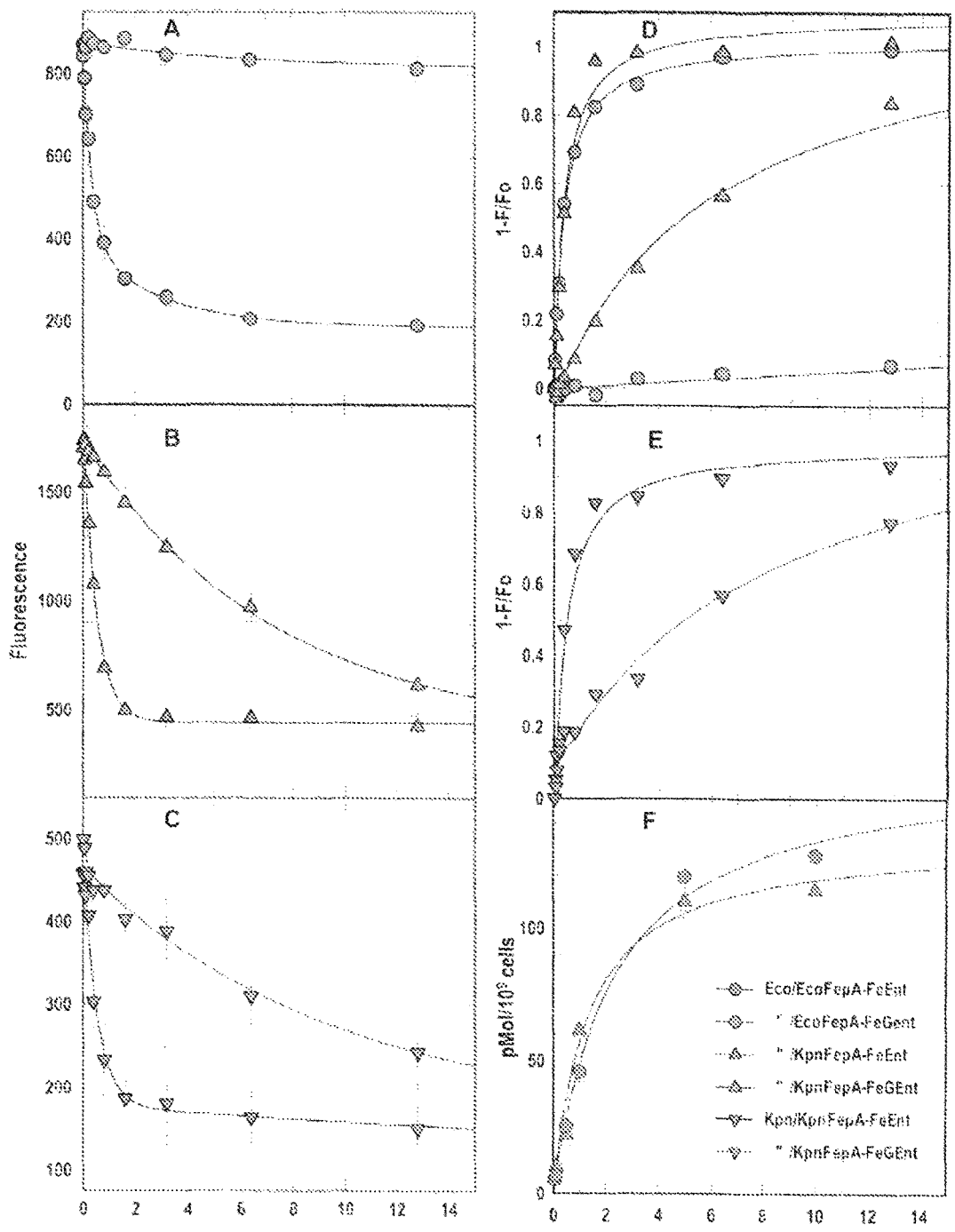
FIG. 5. Binding affinities from spectroscopic assays. (A-E) We added FeEnt (red symbols) or FeGEnt (purple symbols) to *E. coli* OKN13/pEcoFepA-FM (A, D; circles) or OKN13/pKpnFepA-FM (B, D; triangles), or *K. pneumoniae* KKN4/pKpnFepA-FM (C, E; inverted triangles). (A-C) Quenching data from this species-specific test quantified binding of the iron complexes. Non-linear fits of $1-F/F_0$ (D, E) using the 1-site with background equation of Grafit 6.02 revealed the affinities ($K_d$) of the binding reactions (Table 2). (F). [$^{59}$Fe]Ent binding measurements.

Affinity determinations by spectroscopic analyses The analytical capabilities of the fluorescence spectroscopic determinations stood out when we compared the recognition of FeEnt and its glucosylated form, FeGEnt (also known as ferric salmochelin), by EcoFepA and KpnFepA. The ability of Gram (−) pathogens, including *K. pneumoniae*, to glucosylate enterobactin and transport FeGEnt enhances their invasiveness, in part because glucosylation impairs recognition of the iron complex by lipocalins. Additionally, whereas *E. coli* K12 contains a single chromosomal fepA locus that encodes its FeEnt transporter, pathogenic *K. pneumoniae* contain at least three fepA orthologs (chromosomal loci 1658, 4984; plasmid PII locus 0027). IroN of *Salmonella typhimurium* has a role in FeGEnt uptake; its closest ortholog in *K. pneumoniae* is plasmid-mediated fepA0027. After bioinformatic analyses and structural modeling of KpnFepA0027, we cloned its structural gene and engineered Cys substitution T210C (FIG. 2), that is nominally equivalent to T216C in EcoFepA. To define its recognition specificity we expressed and FM-labeled KpnFepA0027_T210C (KpnFepA-FM) in *E. coli* OKN13 ($\Delta$tonB, $\Delta$fepA), and in *K. pneumoniae* KKN4 ($\Delta$entB, $\Delta$fepA0027, $\Delta$fepA1658, $\Delta$fepA4984), relative to EcoFepA-FM in OKN13. The comparison of FeEnt and FeGEnt adsorption to KpnFepA-FM and EcoFepA-FM in different bacteria revealed several things. First, KpnFepA was fluoresceinated to 3-fold higher levels in *E. coli* (FIG. 5B), than in its native *K. pneumoniae* (FIG. 3C). The better labeling of KpnFepA in the *E. coli* sensor strain made it more responsive to quenching, resulting in more accurate measurements (smaller variations in the mean extent of quenching). Second, both KpnFepA-FM and EcoFepA-FM preferred FeEnt ($K_d\approx 0.38$ nM) over FeGEnt ($K_d$=6-280 nM; FIG. 5, Table 2).

TABLE 2

Affinities of EcoFepA and KpnFepA0027 for ferric catecholates.

| | $K_d$ (S.E.) [1] | | | |
|---|---|---|---|---|
| Strain/Species[2] | FeEnt[3] | FeGEnt[3] | Strain/Species[2] | [$^{59}$Fe]Ent[4] |
| OKN13/ pEcoFepA-FM | 0.39 (0.03) | 279 (278) | OKN3/ pEcoFepA | 2.35 (0.68) |
| OKN13/ pKpnFepA-FM | 0.38 (0.07) | 6.26 (0.54) | OKN3/ pKpnFepA | 1.34 (0.03) |
| KKN4/ pKpnFepA-FM | 0.45 (0.12) | 8.57 (2.15) | | |

[1] $K_d$ values were calculated by the 1-site with background equation of Grafit 6.02
[2] Bacteria were grown in iron-deficient minimal MOPS medium to $5 \times 10^8$ cells/mL. For fluorescence studies they were modified with FM, washed with and resuspended in PBS.
[3] Binding determinations were conducted in a 10 mL volume in an OLIS Clarity spectrofluorometer, by adding varying concentrations of purified FeEnt or FeGEnt to bacteria at $1.25 \times 10^7$ cells/mL, and observing quenching. The excitation/emission maxima were 488/520 nm.
[4] [$^{59}$Fe]Ent binding determinations were conducted in 10 mL of ice cold PBS, with cells chilled on ice.

We added varying concentrations of [$^{59}$Fe]Ent to OKN3/ pEcoFepA (circles) or OKN3/pKpnFepA (triangles), measured adsorption of the ferric siderophore by filter binding assays, and obtained non-linear fits to the 1-site with background equation of Grafit 6.02, that gave the affinities ($K_d$) of the binding reactions (Table 2). These data recapitulate previously published affinities and specificities of EcoFepA for FeEnt. FeGEnt adsorbed to KpnFepA with 20-fold lower affinity ($K_d\approx 6.3$ nM) than FeEnt, and FeGEnt barely bound to EcoFepA at all (FIG. 5A), so weakly that it was problematical to make an accurate measurement (Table 2). Despite its 3-fold lower specific fluoresceination in *K. pneumoniae*, KpnFepA-FM showed the same preferences and affinities in that environment (FIGS. 5B,C). Lastly, we compared the spectroscopic tests to conventional radioisotopic binding measurements. The latter approach with [$^{59}$Fe] Ent yielded comparable affinities of EcoFepA and KpnFepA for FeEnt (FIG. 5E, Table 2), but the former fluorescent methods were more sensitive, with equivalent or better reproducibility and more accurate statistical fits (Table 2). Overall, the experiment showed that individual, fluorescently labeled transporters (i.e., the species-specific approach) accurately depicted the concentration dependence of ligand-binding, with best sensitivity in the *E. coli* cell envelope, and less but acceptable accuracy in the more complex cell envelopes of the infectious bacteria.

Figure 7:
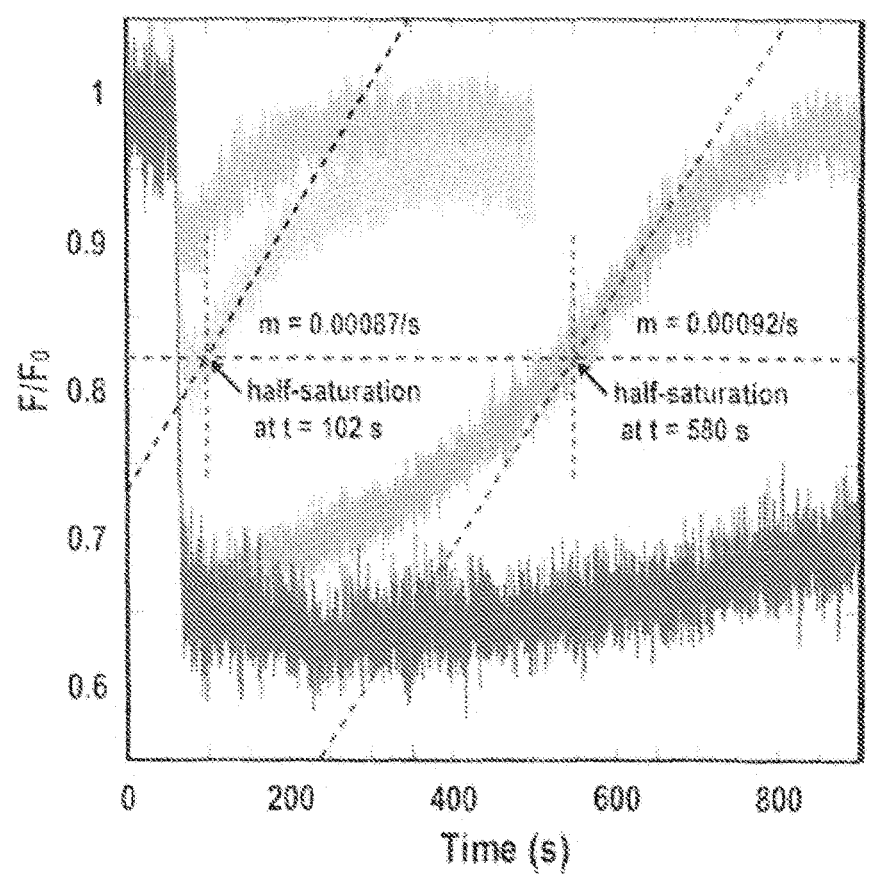
FIG. 7. Uptake rates from FD assays. At t=60 s we added varying concentrations of FeEnt [(0.5 nM (green); 1 nM (yellow); 5 nM (orange); 10 nM (red)] to sensor strain OKN13/pEcoFepA-FM in the presence of test strain *K. pneumoniae* isolate Kp52.145. 10 nM FeEnt gave maximal quenching. For 1 and 5 nM FeEnt, at half-saturation (blue dashed line) we determined the slope of the time course (black dashed line) and the elapsed time (dashed red line). Either parameter estimated the transport rate of the test strain (see text).

Transport rates from spectroscopic analyses. The rate of fluorescence recovery in the spectroscopic system correlates to the rate of ligand depletion by bacterial transport, and comparisons of test strains in universal FD uptake assays reiterated this point. The various ESKAPE bacteria conferred fluorescence recovery at different rates (FIG. 3B). FeEnt binding at 100 s quenched the fluorescence of the FD sensor strain, E. coli OKN13/pEcoFepA-FM. It cannot transport FeEnt, so subsequent recovery did not occur. But, the fluorescence of the E. coli strain reflected FeEnt uptake by other bacteria in the same solution: as they decreased [FeEnt] by cellular transport the intensity of OKN13/pEcoFepA-FM returned to initial levels (as described in FIG. 1B). The assay monitored FeEnt uptake by E. coli expressing chromosomal (Eco; cyan) or plasmid-mediated (Eco/pfepA+; blue) FepA, and ESKAPE species K. pneumoniae (Kpn; red), A. baumannii (Aba; gold), P. aeruginosa (Pae; green), E. cloacae (Ecl; magenta). FepA-deficient K. pneumoniae (KKN4; black) does not transport FeEnt, and did not recover. Hence, OKN13/pEcoFepA-FM was a universal sensor of [FeEnt], that monitored FeEnt acquisition by all the bacteria. Because we tested the individual bacteria at equal cell concentrations, their rates were directly comparable to one another. However, absolute calculations of rate parameters (i.e., $V_{max}$, $k_{cat}$) from FD recovery time courses are complicated by other factors besides the kinetic attributes of the transporters, including their expression levels, and in this system, the expression of TonB. Consequently, FD assays are best suited to comparative rate measurements among the test strains, from either the slope of the recovery curve, or the duration of quenching after initiation of uptake (FIG. 7). In the former case, when uptake of FeEnt reverts fluorescence to a level of 50%, the EcoFepA-FM sensor is half-saturated, so [FeEnt]=$K_d$ (0.38 nM). The slope of the time course at this point reveals the uptake rate of the test strain at [FeEnt]=0.38 nM. In the latter case, the test strain's transport rate determines the elapsed time from addition of FeEnt to half-maximal quenching (i.e., half saturation). For example, at $10^7$ cells/mL K. pneumoniae Kp52.145 required 520 s to deplete 5 nM FeEnt to 0.38 nM (i.e., half-saturation), which translates into a mean uptake rate over the first 520 s of 53 pMol/$10^9$ cells/min. The hypothetical mean uptake rate over this range of saturation (14.3$K_M$>$K_M$) is ~0.8 $V_{max}$, suggesting that for K. pneumoniae Kp52.145, $V_{max}$≈53 pMol/$10^9$ cells/min÷0.8≈66 pMol/$10^9$ cells/min. This value approximates $V_{max}$ for chromosomally expressed FepA in E. coli (50-100 pMol/min/$10^9$ cells). We conducted this prototypic assay with K. pneumoniae in the presence of an E. coli EcoFepA-FM FD sensor, but the test similarly functioned for all of the Gram (−) bacteria (FIG. 3). FD assays are conceptually universal in that an appropriately conFig.d sensor will function in many biological systems, with few exceptions (see the Discussion), to monitor changes in the concentration of its target ligand.

Figure 9:
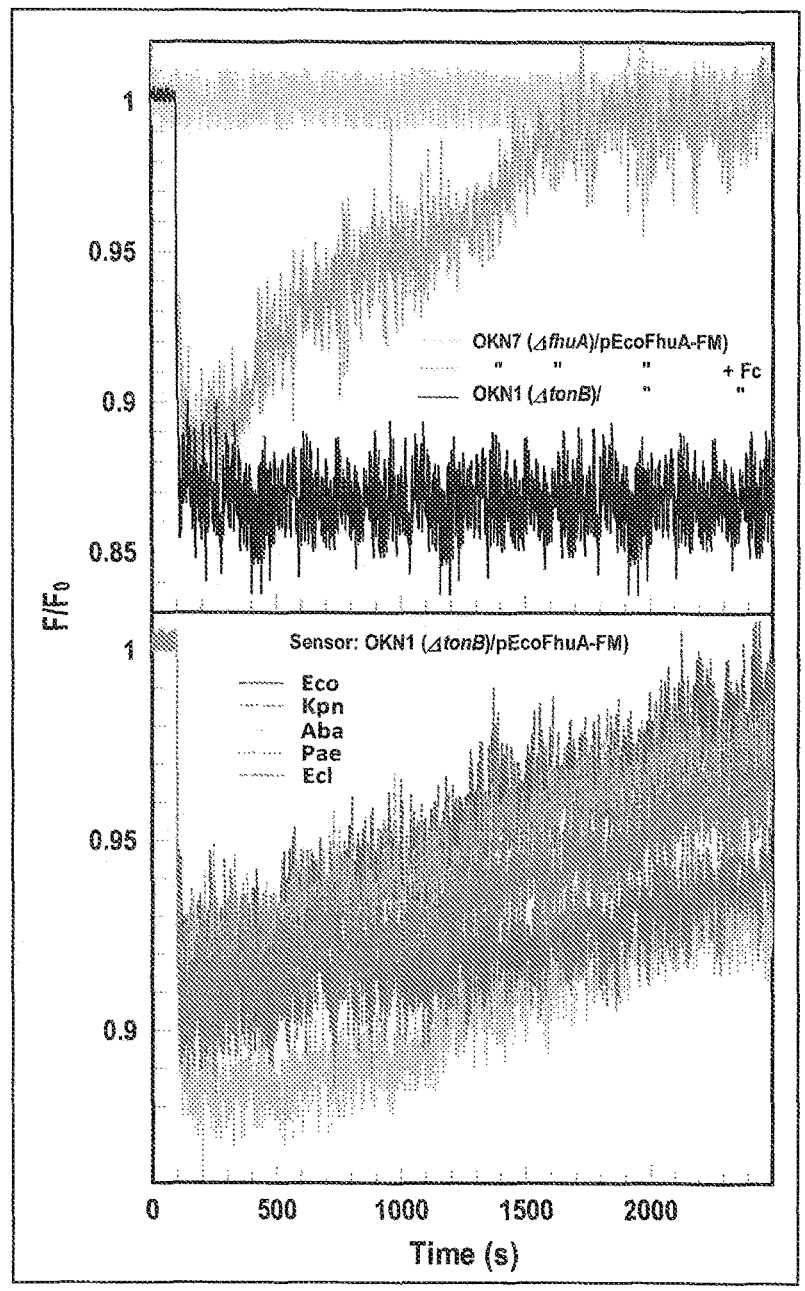
FIG. 9. FD sensor analysis of Fc acquisition by ESKAPE pathogens. (A) Species-specific fluorescence assay of Fc uptake. (B) Universal assay of Fc uptake. The panels show the results of single representative experiments that we performed in triplicate, from which we calculated and plotted the mean values. Standard deviations of the mean measurements (data not shown) were 2.5-4%.

Universal FD sensor of Fc acquisition. The FD sensor approach was relevant to the uptake of other iron complexes, by E. coli and other bacteria. We engineered mutation D396C in EcoFhuA, the OM ferrichrome (Fc) transporter, and modified it with FM (FIG. 2B). EcoFhuA-FM measured Fc uptake in tonB+E. coli (FIG. 9A). OKN7 (4fhuA)/pEcoFhuA-FM reflects Fc binding and transport (orange). In OKN1 (ΔtonB; black) the same construct became an inert sensor of [Fc]: binding of Fc quenched fluorescence, and the absence of transport prevented recovery to initial levels. But, in the TonB-deficient strain OKN1, EcoFhuA-FM was an FD sensor that detected Fc uptake by any of the CRE/ESKAPE bacteria (FIG. 9B). We incubated the sensor strain with 1.5×$10^7$ cells of Gram (−) ESKAPE pathogens. Colored tracings denote the same strains as in FIG. 3. In each case, the pathogens acquired Fc, causing fluorescence recovery of the sensor strain. Uptake of Fc occurred at a slower rate than FeEnt, resulting in slower fluorescence recovery.

As seen for FeEnt-EcoFepA-FM, binding of Fc to EcoFhuA-FM quenched its emissions, and depletion of Fc from solution by microbial transport restored fluorescence intensity. This additional test of a second TonB-dependent transport reaction by the ESKAPE species, without need to genetically modify them, showed the breadth of the FD concept: an appropriately labeled TBDT in a ΔtonB host became a transport-deficient FD sensor cell that reflected the concentration of its ligand in solution. This approach potentially encompasses the diverse repertoire of microbial ferric siderophores and their membrane protein receptors. It is also adaptable to other metal complexes that microbes utilize, and non-metal, high affinity ligand-receptor pairs.

Figure 6:
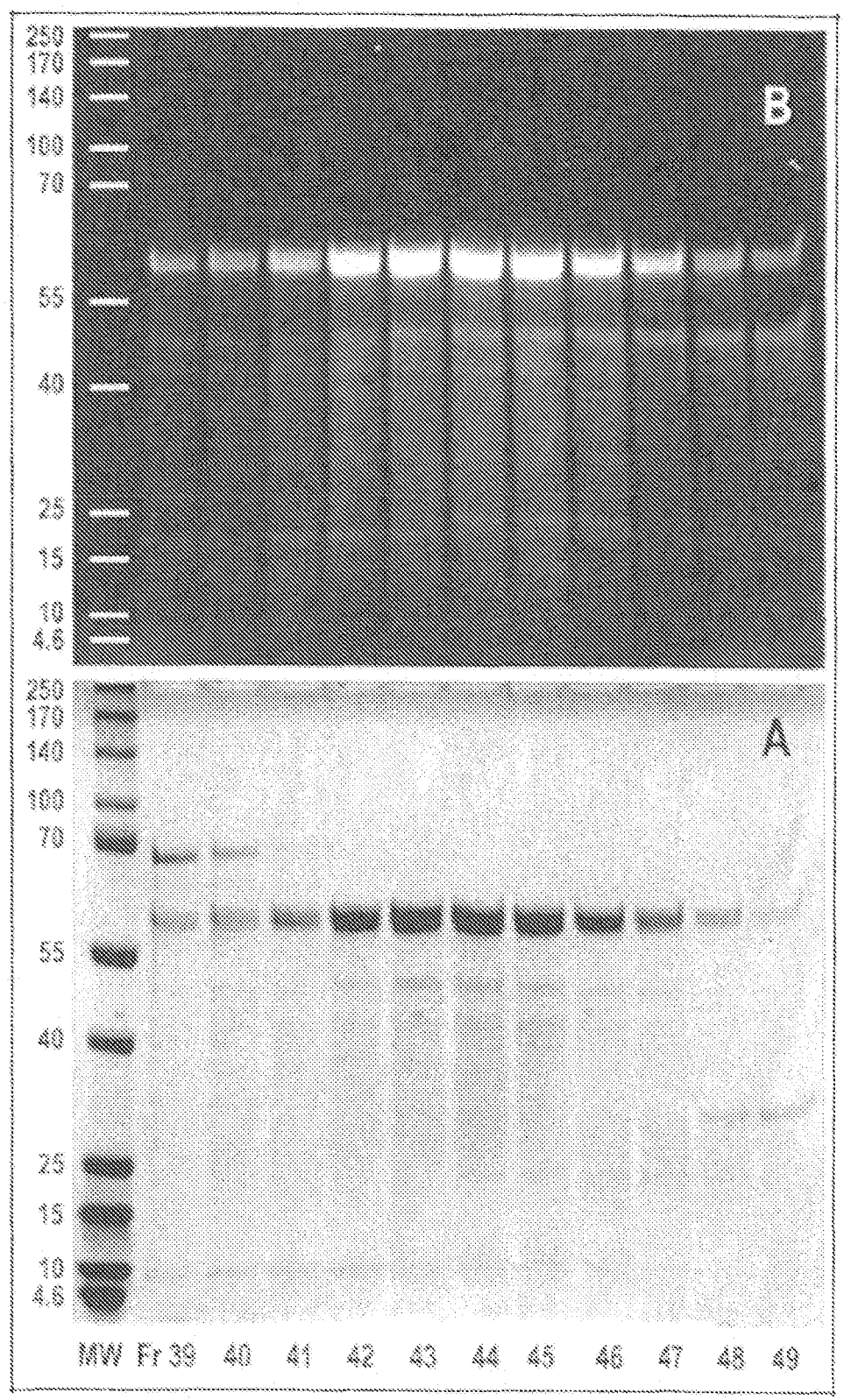
FIG. 6. Purification of LmoHbp2S154C-CPM on Sephacryl S300-HR. (A) Analysis of eluted fractions by SDS-PAGE; and (B) Image of the same gel for fluorescence. The molecular weight markers (MW) in panel B were copied from the mobilities of the protein standards in panel A. We consolidated fractions 42-47 for use in spectroscopic experiments.

Universal FD sensor of heme uptake. Using a slightly modified method, the FD sensor technology described a third relevant microbial transport system: hemin (Hn) uptake by Gram (+) bacteria. Listeria monocytogenes, Staphylococcus aureus, Streptococcus pyogenes, Bacillus anthracis and other Gram (+) bacteria produce NEAT domain-containing Hn-binding proteins, that either anchor to PG by the actions of sortases A and B, or pass to the external environment where they act as hemophores. Some Gram (−) species like Serratia marscescens also secrete hemophores (e.g., HasA), and others (e.g., Vibrio cholerae) directly transport the iron porphyrin. We engineered the listerial NEAT-domain protein Hbp2 to create an FD sensor of Hn binding and uptake (FIGS. 2C, 6). After purifying LmoHbp2S154C and labeling it with CPM, we passed the product over Sephacryl 5300-HR. We analyzed the eluted fractions by SDS-PAGE (Panel A), and imaged the same gel for fluorescence (Panel B; excitation/emission maxima of 384/470 nm).

Figure 10:
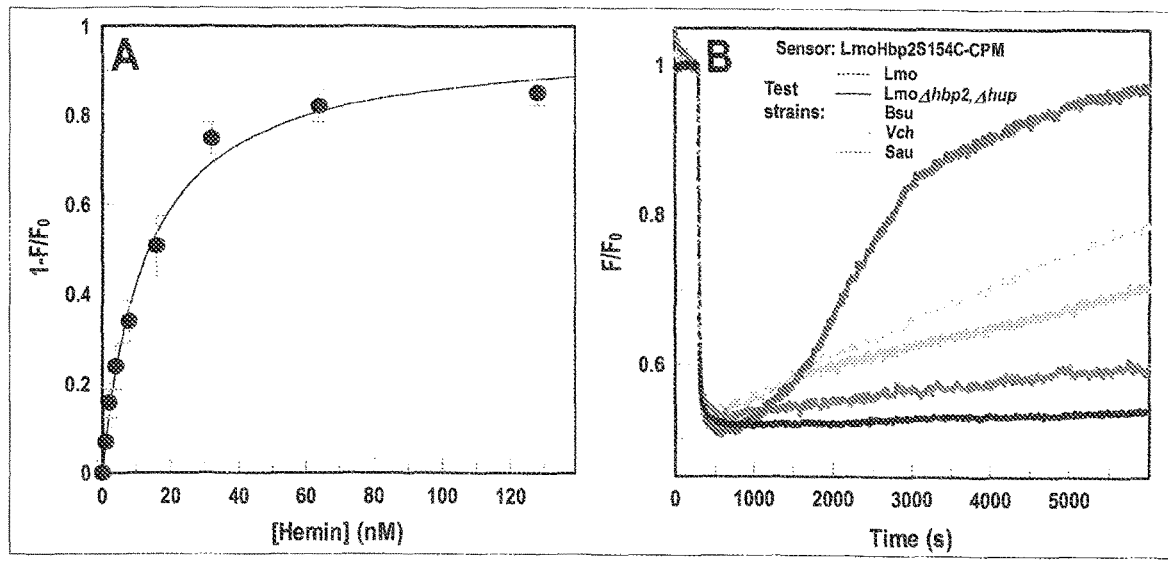
FIG. 10. FD sensor assay of hemin uptake. (A) Concentration-dependence of hemin binding to LmoHbp2-CPM. (B) Hbp2-CPM detects and quantifies bacterial hemin transport. The panel shows the results of single representative experiment that was performed in triplicate, from which we calculated and plotted the mean values. Standard deviations of the mean measurements (data not shown) were 2-2.9%.

We substituted Cys for residue S154 in NEAT1 of LmoHbp2, expressed and purified the binding protein, and covalently modified it with coumarin maleimide (CPM). Introduction of Cys in NEAT-1 of LmoHbp2 allowed its modification by extrinsic fluorophores, transforming the purified binding protein into a sensitive sensor whose emissions inversely related to [Hn]. Using purified LmoHbp2-CPM, plots of 1-F/$F_0$ vs [hemin], analyzed by non-linear fit to the 1-site with background equation of Grafit 6.02, produced a saturation curve with $K_d$=12±3.1 nM. The experiment was performed in triplicate; the mean values, with standard deviations, are shown. LmoHbp2_S154C-CPM (LmoHbp2-CPM) detected Hn in solution (FIG. 10A), with an affinity ($K_d$=12±3.1 nM) that was consistent with isocalorimetric ($K_d$=25–48 nM) and radioisotopic ($K_d$=12 nm) data. The sensor also revealed the ability of other bacteria to transport Hn (FIG. 6B), at different rates. When we mixed Hbp2-CPM with heterologous bacteria in solution, it reflected their hemin uptake. Addition of hemin at 300 s quenched LmoHbp2-CPM emissions, but fluorescence rebounded as bacteria {L. monocytogenes (Lmo; blue), B. subtilis (Bsu; gold), S. aureus (Sau; red), V. cholerae (Vch; green)} transported the porphyrin and depleted it from solution. Conversely, hemin transport-deficient cells (EGDe Δhbp2, Δhup; black) did not elicit fluorescence recovery. Overall, the bacterial cells OKN13/pEcoFepA-FM and OKN1/pEcoFhuA-FM, and the purified protein LmoHbp2-CPM functioned as universal sensors of extracellular iron in different forms: FeEnt, Fc, and hemin, respectively.

Adaptation of FD sensors to fluorescence high-throughput screening (FLHTS). Compounds that block iron acquisition by inhibiting TonB action in Gram (−) bacteria, or by reducing Hn uptake into Gram (+) cells, may combat bacterial proliferation in human and animal hosts. We previously used the species-specific spectroscopic test in microtiter format to screen chemical libraries for inhibitors of E.

coli TonB. Consequently, we transposed the FD sensor assays to microtiter format for FLHTS. However, despite the fact that all the Gram (−) ESKAPE bacteria utilized FeEnt (FIG. 3), the adaptation of this method to screen against them faced obstacles. First, bacterial pathogens often manifest reduced cell envelope permeability that lowers antibiotic susceptibility. Compounds that penetrate E. coli may not enter ESKAPE organisms. Second, protein orthologs in different bacteria typically manifest cross-species sequence divergence, so compounds that inhibit EcoTonB may not similarly impair TonB in Gram (−) ESKAPE bacteria. For these reasons it is preferable to directly screen chemical libraries against the target ESKAPE pathogens. The species-specific approach is adaptable to ESKAPE bacteria for FLHTS (as seen for A. baumannii) and K. pneumoniae (FIG. 3), but more extensive lipopolysaccharides and capsular polysaccharides in clinical isolates reduces the efficiency of modifying their OM proteins with fluorophores (e.g., Kp52.145 in FIG. 5).

Figure 11:
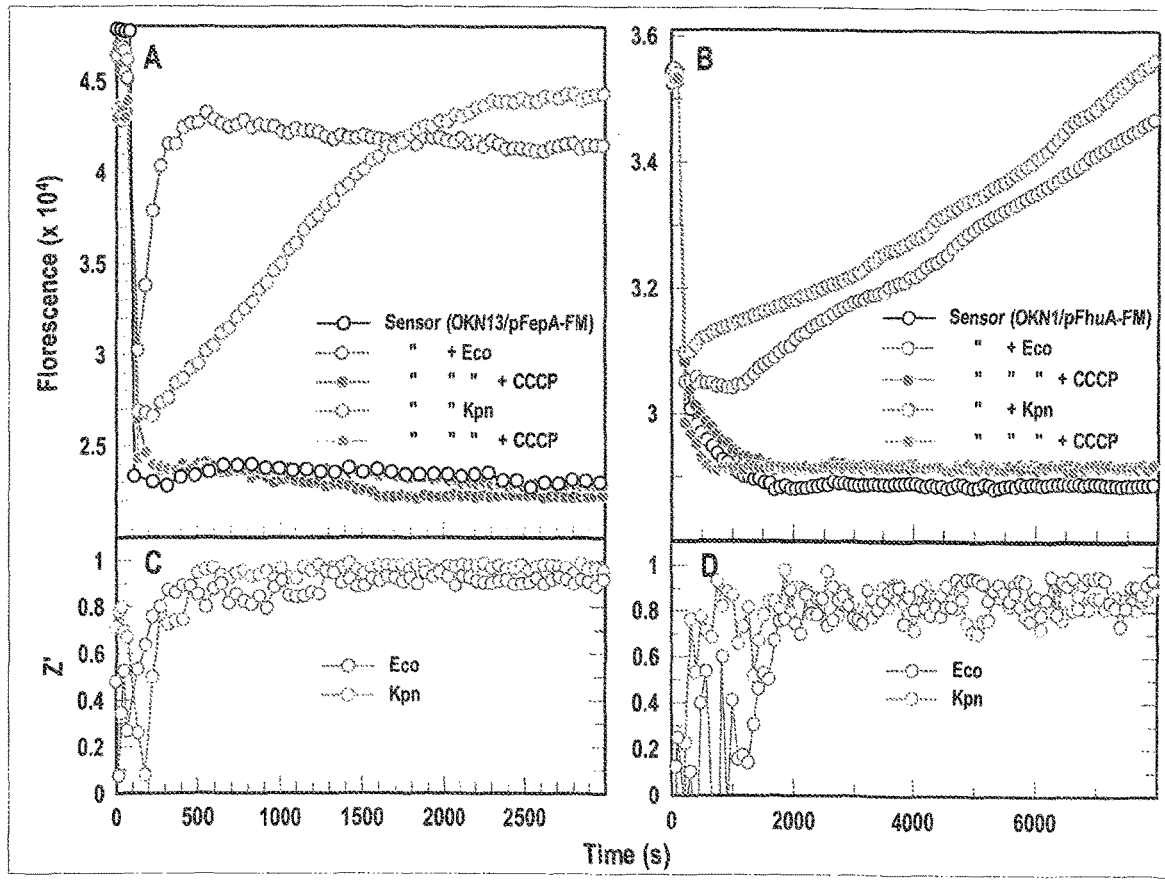
FIG. 11. FD-HTS assay for Gram (−) bacterial TonB-dependent transport of (A) FeEnt using a ΔtonB host harboring pEcoFepA-FM; (B) Fc using a ΔtonB host harboring pEcoFhuA-FM, on microplates; and (C) Z' factors approaching 1.0 within 10 min for FeEnt; and (D) Z' factors approaching 1.0 within 35 min for Fc statistical comparisons of positive and negative controls. The panels show the results of single representative experiments that were performed in triplicate, from which we calculated and plotted the mean values. Standard deviations of the mean measurements (data not shown) were 1.9-4.1%.

FD sensor assays with fluorescent cells or proteins circumvent this problem, because they allow FLHTS against the pathogens (with adequate Z': 0.8-1.0; FIG. 11), without need to fluorescently modify them. We used a ΔtonB host harboring either pEcoFepA-FM or pEcoFhuA-FM, suspended in microtiter plates, to create universal FD sensors of FeEnt or Fc uptake, respectively. The inert sensors effectively monitored active iron transport in 96-well microtiter plates, by both E. coli (blue) and K. pneumoniae (red) (FIG. 11). The proton ionophore CCCP abrogated iron uptake, so fluorescence did not recover in the presence of these compounds. Statistical comparisons of these positive and negative controls yielded Z' factors approaching 1.0, within 10 min in the case of FeEnt (FIG. 11C) and 35 min in the case of Fc (FIG. 11D).

Figure 8:
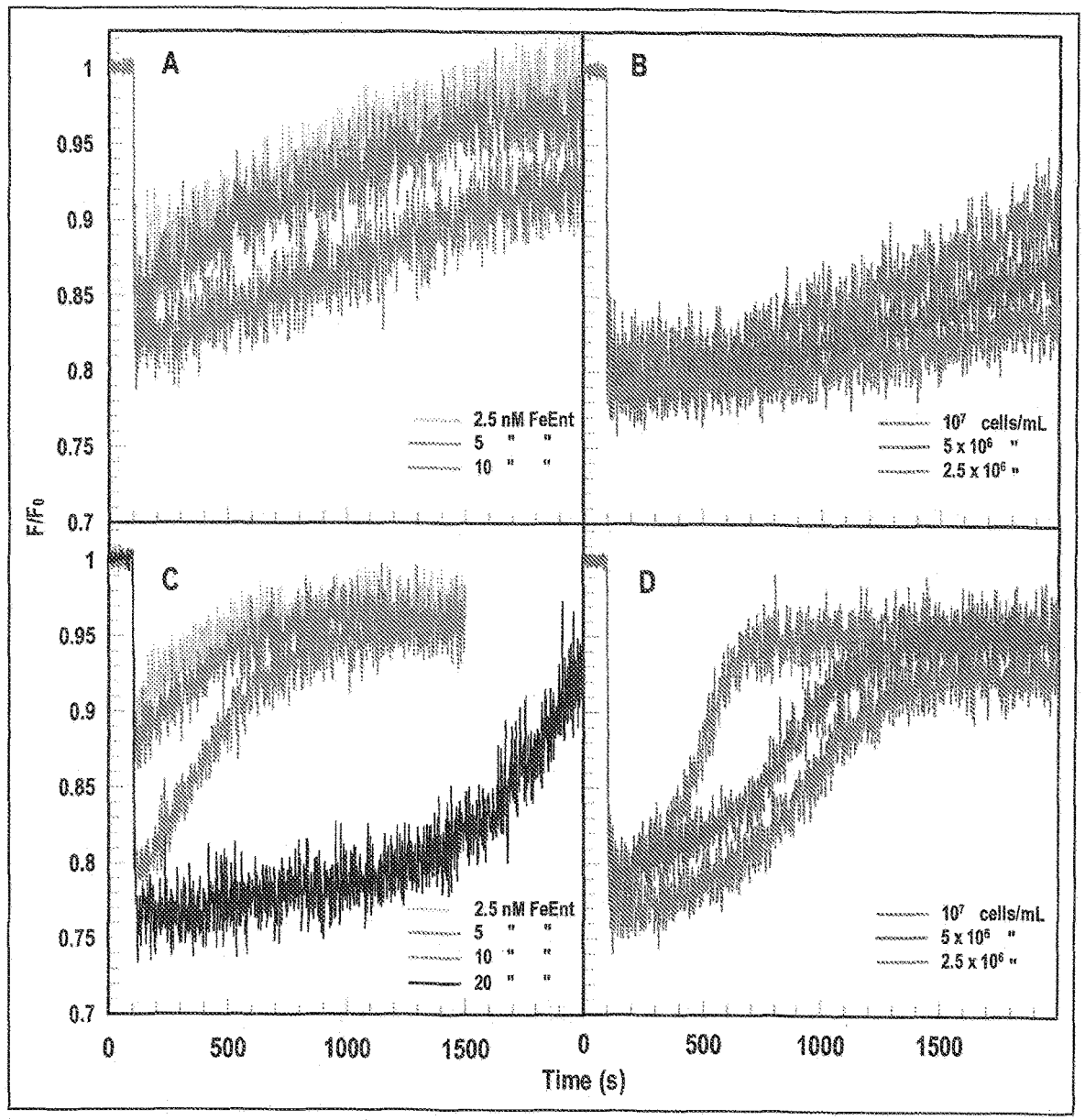
FIG. 8. Effects of FeEnt and cell concentrations on fluorescence recovery. Fluorescence recovery in response to uptake of the ferric siderophore by *K. pneumoniae* KP52145 (Panels A and B) and by *P. aeruginosa* PA01 (Panels C and D). The panels show the results of single representative experiments that were performed in triplicate, from which we calculated and plotted the mean values. Standard deviations of the mean measurements (data not shown) were 2.5-4%.

The E. coli FD sensor cells in microtiter wells followed the TonB-dependent uptake of both FeEnt and Fc by K. pneumoniae. The sensors minimized the experimental manipulations of the pathogen, while allowing spectroscopic observations of its physiology that were sensitive to varying concentrations of both the ligands and the bacterial cells (FIG. 8). Using E. coli OKN13/pFepA-FM as a sensor of [FeEnt], we measured fluorescence recovery in response to uptake of the ferric siderophore by K. pneumoniae KP52145 (Panels A and B) and by P. aeruginosa PA01 (Panels C and D) in solution altered the kinetics of recovery. The FD format responded to ligands in physiologically relevant concentration ranges, using target cell concentrations as low as 106/mL. This sensitivity to the concentrations of its components makes it readily adaptable to macro or micro formats.

DISCUSSION

We considered several attributes of the FD constructs in making the designation "universal." (i) Sensors for FeEnt or Fc or heme had the ability to detect and quantify the uptake of their target ligand by any Gram (+) or (−) bacterium we tested. This unrestricted scope alone strongly supported the term "universal," but FD sensors had additional universalities. (ii) The technical concept was applicable to virtually any high affinity ligand, whether ferric siderophores, other metal complexes, or other molecules. (iii) FD sensors were straightforward to create from any cloned, high affinity binding protein, as we showed for EcoFepA, KpnFepA, EcoFhuA and LmoHbp2. These fluorescently labeled, Cys-mutant proteins detected and discriminated FeEnt, FeGEnt, Fc, and hemin. Hence, it's conceivable to create sensors for any iron complex of interest, or other high affinity ligand. (iv) The site-directed Cys-fluorophore labeling approach succeeded with any maleimide fluorophore we tried: FM, CPM, and in previous work Alexa Fluors 546M, 555M, 647M and 680M, that differ in mass, structure and spectral properties. (v) Because the sensors are expressed from plasmids, engineered BSL-1 sensor strains that host them may be centrally stored and distributed to any interested researcher. (vi) FD sensors may achieve many biochemical and microbiological purposes: determination of the presence and concentrations of siderophores in natural and host environments; identification of the siderophores elaborated, or the ferric siderophores transported by an organism; surveys of microbiological Families, Genera or species to determine which members use a certain metal complex; measurements of the specificities, affinities and kinetic attributes of a transport system, for a single ligand or a family ligands. All these applications have the inherent analytical power to discriminate ligands in the nanomolar concentration range.

A technology that quantitatively monitors (i) any microorganism for uptake of (ii) any specific ligand using (iii) any cloned, high affinity binding protein modified by (iv) any maleimide fluorophore, with (v) central distribution to any investigator for applications that span (vi) a variety of microbiological and biochemical purposes, has a claim to the term "universal." Exceptions or clarifications may arise to this designation, but these may be recognized and stipulated.

The general applicability and technical attributes of FD sensors will aid antibiotic discovery. An HTS plan must include secondary screens and controls to exclude false positives. Fluorescence assays, for example, are susceptible to quenching artifacts that mimic inhibition. FLHTS against TonB was complicated by the involved secondary screening needed to eliminate non-specific quenchers and other irrelevant compounds. However, FD technology enables new fluorescence tests, in microtiter format, that measure the uptake of relevant compounds or identify artifacts. The FD sensor of Fc uptake is one such assay, that may validate or refute the TonB-specificity of primary hits from FeEnt uptake screens. FD sensors of other relevant ligands (vitamin $B_{12}$, ferric aerobactin) are within reach, and each additional test of TonB-dependent transport focuses the experiments on the most valid candidates. FD sensors in FLHTS format permit more rapid screening, allowing expansion of screening programs to larger chemical libraries.

We found that FM modified KpnFepA to higher levels in E. coli than in a clinical isolate of K. pneumoniae, which was a technical advantage. This higher intensity, that likely derived from better fluoresceination in the un-encapsulated, rough laboratory strain, led to better sensitivity to quenching during ligand binding. Consequently, the FD sensor yielded more accurate measurements in E. coli than in K. pneumoniae.

From this work and our experience with binding determinations, fluorescence studies are faster, simpler, more sensitive, more reproducible and less hazardous than radioisotopic experiments. Optimum measurements of [$^{59}$Fe]Ent-FepA affinity require a large assay volume (~25 mL) to avoid substrate depletion at low concentrations, and [$^{59}$Fe] with high specific radioactivity. The short half-life of the isotope (44.6 d) results in rapid loss of sensitivity. Fluorescence binding assays are not confounded by such problems, because of the high intensity and environmental sensitivity of selected fluorophores (e.g., FM). Our fluorescent sensors reported higher affinities ($K_d$=0.4 nM; Table 2) than the [$^{59}$Fe]Ent-EcoFepA binding studies ($K_d$=1-2 nM). The spectroscopic tests were also most consistent with previous determinations ($K_d$=0.2–0.5 nM).

FD sensor assays are not undermined by adventitious iron, nor by siderophores secreted by test bacteria. We supplied chelated iron, as FeEnt, Fc or Hn, for transport by the target cells. Neither extraneous $Fe^{++}$ nor $Fe^{+++}$ interfere, because FepA, FhuA and Hbp2 have no affinity for unchelated iron. FD sensor cells carry mutations that block siderophore production. Aposiderophores from the test cells (e.g., enterobactin, aerobactin, acinetbactin, etc.) may bind adventitious iron in the assay buffers, but we curtail this problem by washing cells before analysis, to remove any associated siderophores. The relatively short FD assay duration (<30 min) minimizes siderophore production by the test bacteria, that generally requires extended growth in iron-deficient media for secretion of substantial amounts. The FD assay buffer (PBS+0.2% glucose) contains little adventitious iron and no metabolites, so it constrains biosynthesis by the test bacteria.

Experimental Procedures

Bacteria, plasmids, genetic engineering and cell growth. *E. coli* strains descended from BN1071 (entA): OKN1 (ΔtonB), OKN3 (ΔfepA), OKN7 (ΔfhuA), and OKN13 (ΔtonB, ΔfepA). ESKAPE strains included *K. pneumoniae* Kp52.145 (courtesy of Regis Tournebiz, Institut Pasteur), *A. baumannii* ATCC 17978, *P. aeruginosa* PA01 (courtesy of Stephen Lory, Harvard University) and *Enterobacter cloacae*. *K. pneumoniae* KKN4 originated from Kp52.145 by sequential site-directed deletions of entB and three annotated kpnfepA structural genes: chromosomal loci 1658 and 4984, and plasmid (pII) locus 0027. The resultant mutant strain did not synthesize nor secrete enterobactin, nor transport ferric catecholate iron complexes. However, it was an effective host for plasmids carrying fepA alleles.

Figure 4:
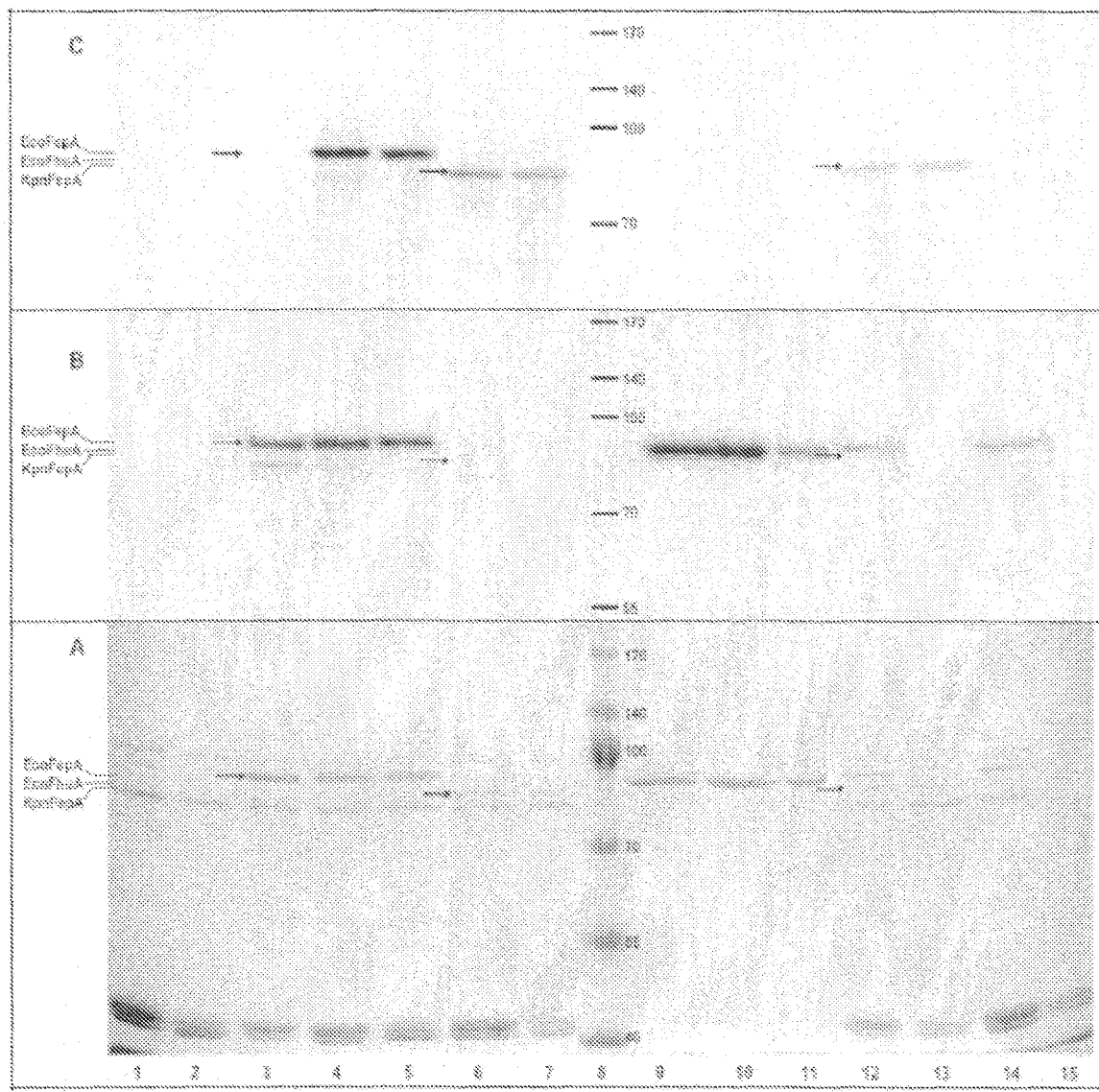
FIG. 4. Fluorescence labeling of EcoFepA, KpnFepA and EcoFhuA Cys mutants in living bacteria. (A) SDS-PAGE gel of cell envelope samples (30 ug), stained with coomassie blue. Lane 1: *E. coli* OKN3 (ΔfepA); 2: *E. coli* OKN13 (ΔtonB, ΔfepA); 3: OKN3/pEcoFepA); 4: OKN3/pEcoFepAA698C-FM; 5: OKN13/pEcoFepAA698C-FM; 6: OKN3/pKpnFepAT210C-FM; 7: OKN13/pEcoFepAA698C-FM; 8: mw markers; 9-11: 3, 2, 1 ug of EcoFepA; 12: *E. coli* OKN7 (fhuA)/pFhuAS394C-FM; 13: OKN13/pFhuAS394C-FM; 14: OKN7; 15: OKN13/pFhuA. (B) Western immunoblot of a duplicate gel with anti-FepA MAbs 41 and 45, developed with [$^{125}$I]— protein A. (C) Fluorescence scan (excitation 488 nm/emission 520 nm) of an identical gel. Despite different expression levels (EcoFepAA698C>KpnFepAT210C>EcoFhuAS394C) the labeling procedures exclusively and selectively modified the FepA or FhuA Cys mutants. Other cell envelope proteins, and wild-type TBDT (lanes 1-3, 14, 15) were not labeled by FM.

Cys mutant proteins. To generate Cys substitution mutants of FepA and FhuA we used QuikChange mutagenesis (Agilent) of the wild type genes on pITS23 and pITS11, respectively. Both plasmids derived from the low-copy plasmid pHSG575. pEcoFepA_A698C is a pITS23 derivative with the engineered substitution A698C; pITS11 hosts wild-type ecofhuA; pEcoFhuA_D396C is a pITS11 derivative with the engineered mutation D396C (this study). pKpnFepA_T210C is a pHSG575 derivative that encodes KpnFepA (allele 0027) under control of its native promoter, with the engineered substitution T210C (this study). For structural predictions of KpnFepA, which has 82% identity to EcoFepA, we relied on the guideline that >25% sequence identity strongly predicts an overall identical protein fold. To determine labeling targets in KpnFepA, we performed a CLUSTALW alignment against EcoFepA (PDB sequence 1FEP), and used the Modeller function of CHIMERA (UCSF) to predict its tertiary structure, including surface loops. Cells expressing T210C, located in L2, were quantitatively modified by fluorescein-5-maleimide (FM; FIG. 4). Briefly, *E. coli* strains expressing EcoFepA, KpnFepA, or EcoFhuA with site-directed Cys substitutions were grown in MOPS media, labeled with FM, and fractionated to obtain cell envelopes.

To generate Cys mutants in LmoHbp2, we cloned the hbp2 structural gene (lmo2185) in pAT28, introduced Cys substitutions at positions of interest by QuikChange mutagenesis, and verified the mutations by DNA sequencing. We transformed the pAT28 derivative pLmoHbp2_S154C into *L. monocytogenes* EGDeΔhbp2, grew the strain to late exponential phase in iron-deficient MOPS-L media and purified the secreted Cys mutant protein from iron-deficient bacterial cultures. After removing the cells by centrifugation we precipitated secreted Hbp2_S154C from the supernatant with 0.6 M neutralized trichloroacetic acid, collected the precipitate at 10,000×g for 30 min, washed the precipitated protein with 70% acetone, then washed it with, and resuspended it in 50 mM $NaHPO_4$, at pH 6.7.

Fluorescence modifications of Cys-mutant proteins. We inoculated OKN3, OKN11, OKN13 and KKN4, harboring plasmids and expressing Cys mutant FepA proteins, from frozen stocks into LB broth, grew them overnight and subcultured at 1% into iron-deficient MOPS minimal media, with shaking (200 rpm) at 37° C. for 6-7 h, until late exponential phase. We labeled Cys-mutant FepA proteins in these strains with 5 uM FM in 50 mM $NaHPO_4$, pH 6.7 for 15 min at 37° C. FM.

We labeled LmoHbp2_S154C with 5 uM 7-diethylamino-3-(4'-maleimidylphenyl)-4-methyl coumarin (CPM) in 50 mM $NaHPO_4$, pH 6.7 for 30 min at 37° C., precipitated the reaction mixture with 70% acetone, and collected LmoHbp2-CPM by centrifugation at 10,000×g for 20 min. We chromatographically purified LmoHbp2-CPM over Sephacryl S-300HR in PBS (FIG. 6) and consolidated fractions 42-47 for spectroscopic studies. In all experiments with Hbp2 and Hn, we took precautions to maximize the solubility of the porphyrin: fresh solutions of Hn formulated in DMSO and dispensed to physiological concentrations in alkaline buffers.

Fluorescence spectroscopy. We observed fluorophore-labeled cells in an SLM AMINCO 8100 fluorescence spectrometer, upgraded with an OLIS operating system and software (OLIS SpectralWorks, OLIS Inc., Bogart, GA), to control its shutters, polarizers and data collection. We also utilized an OLIS Clarity fluorescence spectrometer for fluorescence assays of ferric catecholate binding.

Species-specific fluorescence assay of FeEnt uptake: KpnFepA-FM. *E. coli* OKN3 (ΔfepA) expressing KpnFepA-FM was exposed to FeEnt in PBS+0.2% glucose. For species-specific ferric siderophore transport assays of Gram (–) bacteria we added an iron complex to $2 \times 10^7$ labeled cells in a quartz cuvette (final volume, 2 mL) with stirring at 37° C., and monitored the time course of fluorescence emissions at 520 nm. For FD assays, we incubated $1 \times 10^7$ sensor cells and $1.5 \times 10^7$ cells of test organisms (*E. coli* MG1655, *K. pneumoniae* Kp52.145 or KKN4, *A. baumannii* 17878, *P. aeruginosa* PA01, *E. cloacae*) together in 2 mL of PBS+0.4% glucose, at 37° C., in a quartz cuvette. After addition of the ferric siderophore, we monitored the time-course of fluorescence emissions at 520 nm for 15-30 minutes, with stirring. FD assays in microtiter plates contained $4 \times 10^6$ FD sensor cells and $3 \times 10^6$ cells of test organisms (*E. coli* MG1655 or *K. pneumoniae* Kp52.145), in 200 µL of PBS+0.4% glucose at 37° C. We monitored quenching and recovery of fluorescence by ferric siderophores added to a final concentration of 5 nM, in presence or absence of ionophore carbonyl cyanide m-chlorophenyl hydrazone (CCCP).

For fluorescence spectroscopic determinations of Gram (+) bacterial heme acquisition we used the FD sensor LmoHbp2_S154C-CPM. We determined its affinity for Hn by titrations of 30 nM LmoHbp2_S154C-CPM with 1-255 nM hemin, while monitoring fluorescence in the an SLM-OLIS fluorimeter at excitation/emission wavelengths of 390/480 nm, and plotted the ensuing fluorescence quenching with Grafit 6.012 (Erithacus Ltd, Middlesex UK). For measurements of Hn uptake by heterologous bacteria we suspended the LmoHbp2_S154C-CPM sensor protein at 30 nM in PBS+0.2% glucose in a 2 mL cuvette, added Hn to 15 nM after 300 s, and then added iron-starved bacterial cells at 600 s, to a final concentration of 5×10$^7$/mL, and monitored fluorescence for 2 h.

When collecting fluorescence spectroscopic data of bacterial transport processes we performed each experiment at least 3 times, and repeated each individual time course or condition within an experiment in triplicate. We calculated the mean values and standard deviations of the triplicate measurements and plotted the resulting data with Grafit 6.02.

Example 2

Figure 12:
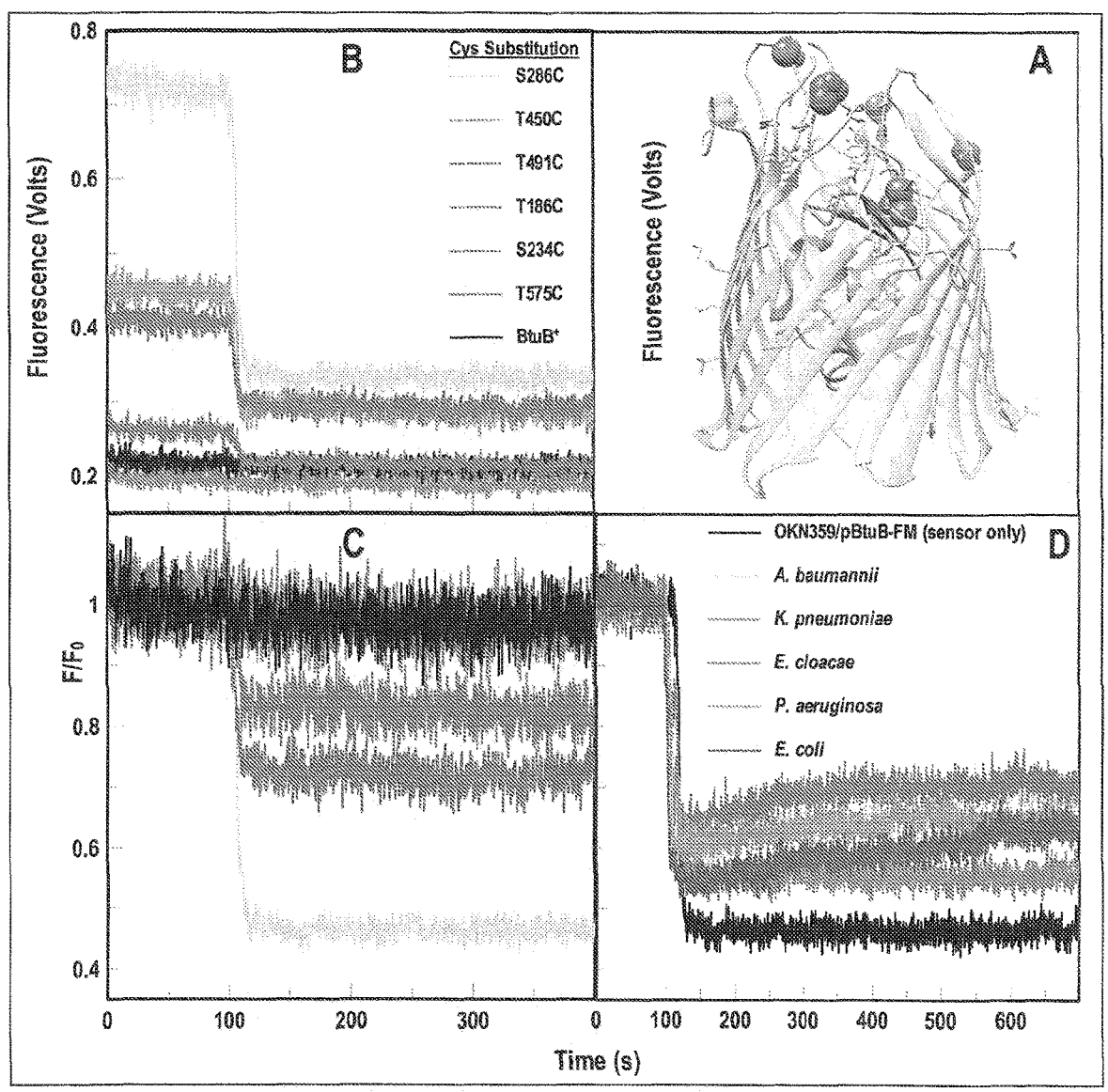
FIG. 12. FD sensor (EcoBtuB) for vitamin B12. We cloned the btuB gene of *E. coli*, mutagenized it to insert Cys residues at sites of interest in protein BtuB (panel A, colored residues), then labeled each site individually with fluorescein maleimide (FM) and evaluated the binding of 20 nM vitamin $B_{12}$ by the extent of fluorescence quenching (panel B: raw data; panel C: normalized data).

Using the same procedures outlined above, we developed FD sensors for ferric aerobactin (KpnIutA) and vitamin B12 (EcoBtuB). The results are in FIG. 12 and demonstrate the activity of the fluorescent B12 sensor protein. We cloned the btuB gene of *E. coli*, mutagenized it to insert Cys residues at sites of interest in protein BtuB (panel A, colored residues), then labeled each site individually with fluorescein maleimide (FM) and evaluated the binding of 20 nM vitamin B12 by the extent of fluorescence quenching (panel B: raw data; panel C: normalized data). The experiment revealed that site S286C (yellow) was optimum for observation of vitamin B12 binding. Panel D shows the uptake of vitamin B12 by Gram (−) ESKAPE pathogens and *E. coli*, using residue S286C as a universal fluorescent sensor.

The invention claimed is:

1. A universal bacterial assay for detecting and monitoring changes in concentration of a target analyte in solution, said assay comprising:
creating a reaction solution comprising a transport-deficient high affinity protein-based sensor and a test bacteria dispersed in an aqueous solution, wherein the sensor comprises a transport-deficient bacterial high affinity binding protein modified with a detectable label that generates a detectable signal;
adding a target analyte to said reaction solution, wherein said high affinity binding protein is specific for binding with said target analyte but transport-deficient, and wherein said target analyte is a metal or metallated complex;
exposing said reaction solution to an energy source to generate said detectable signal; and
detecting changes in the detectable signal in the reaction solution over time, wherein said changes correspond to interaction of said test bacteria with said target analyte.

2. The assay of claim 1, wherein said transport-deficient high affinity binding protein comprises an amino acid residue that has been modified with a detectable label.

3. The assay of claim 2, wherein said modified amino acid residue consists of a cysteine substitution, wherein said detectable label is attached to said cysteine residue.

4. The assay of claim 1, wherein said sensor consist of said modified high affinity binding protein as a purified protein.

5. The assay of claim 1, wherein said sensor is a transport-deficient bacterial cell expressing said modified high affinity binding protein.

6. The assay of claim 5, wherein said transport-deficient bacterial cell is a Gram-negative bacteria selected from the group consisting of *Acinetobacter baumannii*, *Klebsiella pneumoniae*, *Pseudomonas aeruginosa*, *Enterobacter aerogenes*, and *Escherichia coli*.

7. The assay of claim 1, wherein said high affinity binding protein is selected from the group consisting of EcoFepA, EcoFhuA, EcoBtuB, KpnIutA, KpnIroN, LmoHbp2, CcrHutA, modified with a cysteine substitution.

8. The assay of claim 1, wherein said detectable label is a fluorophore.

9. The assay of claim 8, wherein said fluorophore is a maleimide fluorophore.

10. The assay of claim 9, wherein said maleimide fluorophore is fluorescein maleimide, CPM, Alexa Fluors 488, 546, 555, 647, 680, and 720.

11. The assay of claim 1, wherein said reaction solution has a total volume of less than about 300 μL total solution.

12. The assay of claim 1, wherein adding said target analyte comprises adding a source of iron or iron complex to said reaction solution.

13. The assay of claim 12, wherein said analyte is chelated iron or siderophore, ferric enterobactin, ferrichrome, ferric aerobactin, or hemin.

14. The assay of claim 1, wherein said analyte is vitamin B12.

15. The assay of claim 1, wherein said changes in the detectable signal comprise quenching of said detectable signal as said target analyte is bound by said sensor.

16. The assay of claim 15, wherein said changes further comprise unquenching of said detectable signal as said target analyte is taken up by said test bacteria and depleted from said reaction solution.

17. The assay of claim 15, said assay further comprising adding a candidate compound to said reaction solution before said target analyte, wherein said changes correspond to the effect of said candidate compound on interaction of said test bacteria with said target analyte.

18. The assay of claim 17, wherein said candidate compound inhibits said test bacteria from taking up said target analyte, wherein said detectable signal remains quenched.

19. The assay of claim 1, said assay comprising a first reading comprising:
exposing said reaction solution to said energy source to generate said detectable signal before adding said target analyte; and
detecting an initial detectable signal.

20. The assay of claim 19, said assay further comprising a second reading comprising:
exposing said reaction solution to said energy source to generate said detectable signal immediately after adding said target analyte; and
detecting an intermediate detectable signal, wherein a decrease in intensity of said intermediate detectable signal as compared to said initial detectable signal indicates binding of said target analyte to said sensor.

21. The assay of claim 20, said assay further comprising a third reading comprising:
exposing said reaction solution to said energy source to generate said detectable signal at least 5 minutes after adding said target analyte to said reaction vessel; and
detecting a final detectable signal, wherein an increase in intensity of said final detectable signal as compared to said intermediate detectable signal indicates transport of said target analyte by said test bacteria, and wherein a lack of increase in intensity of said final detectable signal as compared to said intermediate detectable signal indicates a transport deficiency in said test bacteria.

22. The assay of claim 1, wherein said assay is a high-throughput screening method, further comprising distributing said reaction solution into a plurality of individual reaction vessels, each vessel comprising respective reaction volumes.

23. The assay of claim 22, wherein said distributing comprises:
   depositing said high affinity protein-based sensor and test bacteria in an aqueous solution in a reaction vessel;
   adding a target analyte to said reaction vessel; and
   incubating said target analyte with said high affinity protein-based sensor and test bacteria for a period of time.

24. The assay of claim 23, wherein each reaction vessel is a microwell in a multi-compartment microplate.

25. The assay of claim 24, wherein a plurality of different test bacteria are added to respective microwells on said microplate.

26. The assay of claim 24, wherein said microplate is a 96-, 384-, or 1536-compartment microplate.

27. The assay of claim 24, further comprising adding a candidate compound to said microwells.

28. The assay of claim 27, wherein a plurality of different candidate compounds are added to respective microwells on said microplate.

29. A kit for conducting universal bacterial assay for detecting and monitoring changes in concentration of a target analyte in solution, said kit comprising:
   a transport-deficient high affinity protein-based sensor comprising a transport-deficient high affinity binding protein modified with a detectable label that generates a detectable signal, wherein said high affinity binding protein is a bacterial protein specific for binding with a metallated target analyte but transport-deficient;
   optionally, an amount of said target analyte;
   instructions for creating a reaction solution with said transport-deficient high affinity protein-based sensor, a test bacteria strain, and said target analyte;
   instructions for exposing said reaction solution to an energy source to generate said detectable signal; and
   instructions for detecting changes in the detectable signal in the reaction solution over time to determine the interaction of said test bacterial strain with said target analyte.

30. The kit of claim 29, wherein said sensor is a transport-deficient bacterial cell expressing said modified high affinity binding protein.

* * * * *